United States Patent
Biermann et al.

(10) Patent No.: US 11,877,983 B2
(45) Date of Patent: Jan. 23, 2024

(54) DETECTION SYSTEM FOR FLOW CONTROL APPARATUS

(71) Applicant: KPR U.S., LLC, Mansfield, MA (US)

(72) Inventors: Wayne T. Biermann, Hazelwood, MO (US); John H. Holste, Hazelwood, MO (US)

(73) Assignee: KPR U.S., LLC, Mansfield, MA (US)

( * ) Notice: Subject to any disclaimer, the term of this patent is extended or adjusted under 35 U.S.C. 154(b) by 235 days.

(21) Appl. No.: 17/328,556

(22) Filed: May 24, 2021

(65) Prior Publication Data
US 2021/0361534 A1 Nov. 25, 2021

Related U.S. Application Data

(60) Provisional application No. 63/028,951, filed on May 22, 2020.

(51) Int. Cl.
*A61J 15/00* (2006.01)
*A61M 5/168* (2006.01)
*A61M 5/142* (2006.01)

(52) U.S. Cl.
CPC ....... *A61J 15/0088* (2015.05); *A61J 15/0076* (2015.05); *A61M 5/14212* (2013.01); *A61M 5/16804* (2013.01); *A61M 5/16854* (2013.01); *A61M 2005/16863* (2013.01); *A61M 2205/3331* (2013.01); *A61M 2205/3334* (2013.01); *A61M 2205/3375* (2013.01); *A61M 2205/50* (2013.01)

(58) Field of Classification Search
CPC ... G01F 1/667; A61J 15/0088; A61J 15/0076; A61M 5/14212; A61M 5/16804; A61M 5/16854; A61M 2005/16863; A61M 2205/3331; A61M 2205/3334; A61M 2205/3375; A61M 2205/50
See application file for complete search history.

(56) References Cited

U.S. PATENT DOCUMENTS

| | | |
|---|---|---|
| 7,373,839 B2 | 5/2008 | Wiest et al. |
| 8,347,734 B2 | 1/2013 | Berger et al. |
| 8,356,523 B2 | 1/2013 | Berger et al. |
| 8,757,006 B2 | 6/2014 | Berger et al. |
| 9,612,141 B2 | 4/2017 | Ryu et al. |
| 9,618,371 B2 | 4/2017 | Muraki |

(Continued)

OTHER PUBLICATIONS

International Search Report issued by the International Search Authority in related International Application No. PCT/US2017/033847, dated Sep. 9, 2021.

*Primary Examiner* — James D Ponton
(74) *Attorney, Agent, or Firm* — ArentFox Schiff LLP

(57) ABSTRACT

A flow control apparatus comprising a housing capable of receiving a portion of the feeding set, a pumping device configured to receive the feeding set and may produce a fluid flow in the feeding set and deliver fluid to a subject, an ultrasonic sensor may be configured to produce a sensor signal indicative of a condition of the feeding set, and a control circuit in communication with the ultrasonic sensor for receiving the sensor signal from the ultrasonic sensor indicative of the condition of the feeding set. The ultrasonic sensor may comprise a plurality of sensor components which may be configured to emit an ultrasonic signal in a first direction, and in a second direction opposite the first direction through the feeding set.

25 Claims, 19 Drawing Sheets

(56) References Cited

U.S. PATENT DOCUMENTS

| | | | |
|---|---|---|---|
| 10,151,618 B2 | 12/2018 | Birtcher et al. | |
| 2002/0062690 A1* | 5/2002 | Kobayashi | G01F 1/74 73/204.27 |
| 2005/0288873 A1* | 12/2005 | Urdaneta | G01F 1/66 137/487.5 |
| 2010/0024570 A1* | 2/2010 | Berger | G01F 1/667 73/861.27 |
| 2015/0093307 A1* | 4/2015 | Gaines | F04B 51/00 422/554 |

* cited by examiner

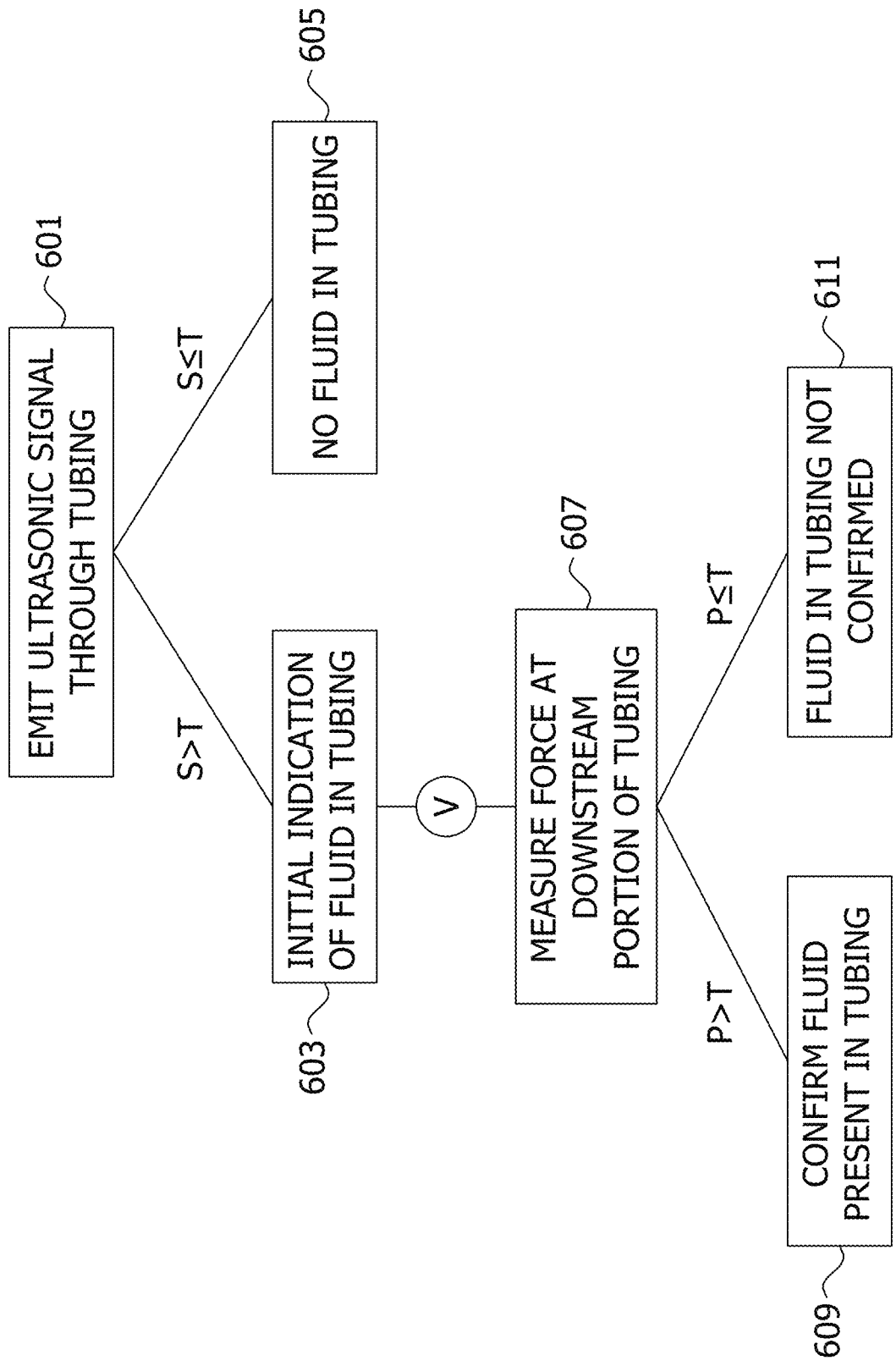

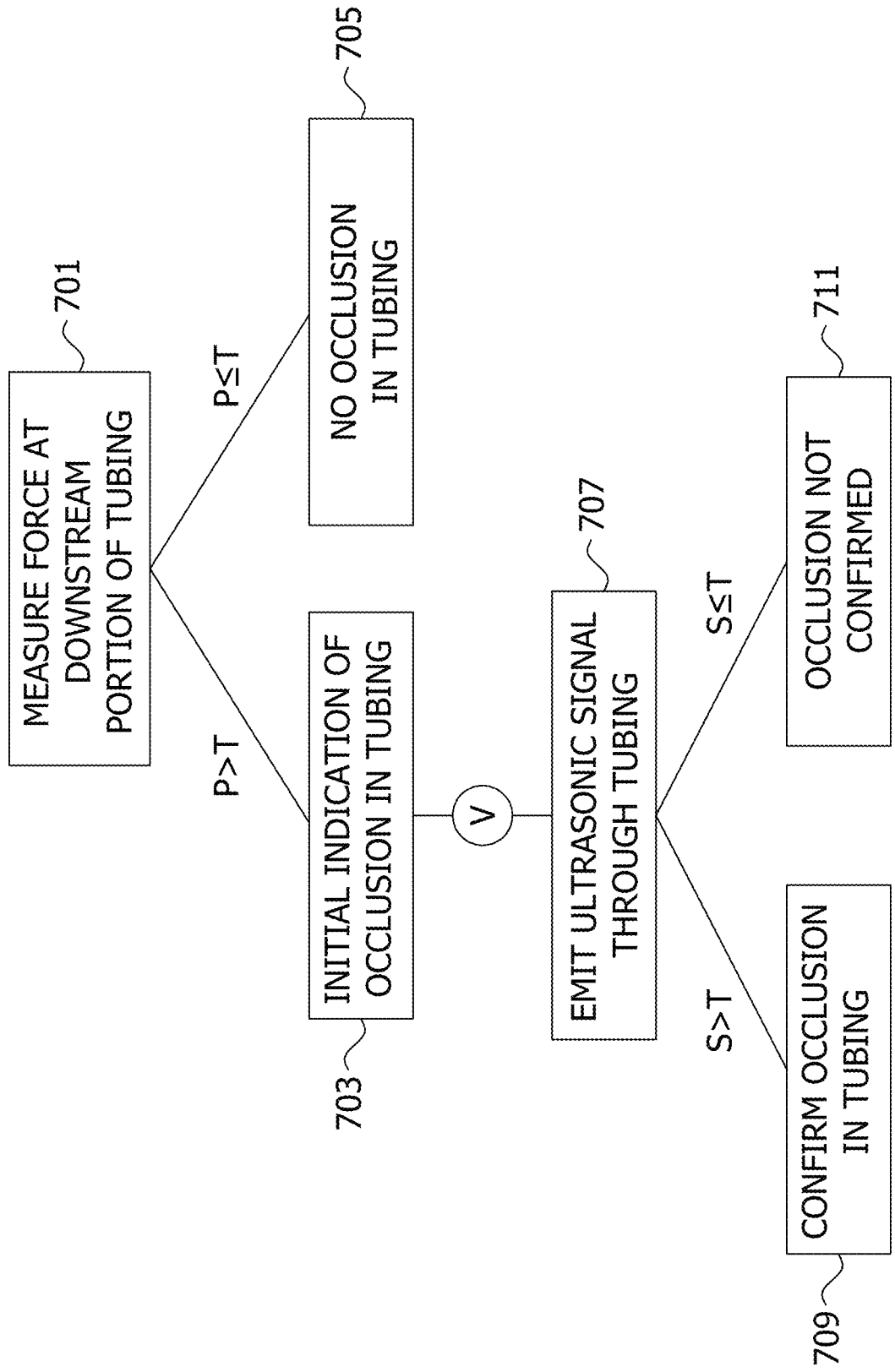

| Rule | | | | % |
|---|---|---|---|---|
| 1 | 358 | 494 | 136 | 27.53% |
| 2 | 597 | 984 | 387 | 39.33% |
| 3 | 65 | 85 | 20 | 23.53% |
| 4 | 1259 | 831 | 428 | 34.00% |
| 5 | 1374 | 837 | 537 | 39.08% |
| 6 | 494 | 627 | 133 | 21.21% |
| 7 | 1298 | 772 | 526 | 40.52% |
| 8 | 352 | 512 | 160 | 31.25% |
| 9 | 2356 | 2183 | 173 | 7.34% |
| 10 | 1110 | 682 | 428 | 38.56% |

FIG. 13A

| Run | Switch Pos. A | Switch Pos. B (Connect) | Delta | % |
|---|---|---|---|---|
| 1 | 674 | 419 | -255 | -60.9 |
| 2 | 650 | 600 | -50 | -8.3 |
| 3 | 543 | 510 | -33 | -6.5 |
| 4 | 790 | 805 | 15 | 1.9 |
| 5 | 670 | 618 | -52 | -8.4 |

| Run | Switch Pos. A | Switch Pos. B (Connect) | Delta | % |
|---|---|---|---|---|
| 1 | 1100 | 1079 | -21 | -1.9 |
| 2 | 1222 | 1102 | -120 | -10.9 |
| 3 | 1235 | 1097 | -138 | -12.6 |
| 4 | 1017 | 803 | -214 | -26.7 |
| 5 | 1093 | 941 | -152 | -16.2 |

| Run | Switch Pos. A | Switch Pos. B (Connect) | Delta | % |
|---|---|---|---|---|
| 1 | 248 | 73 | -175 | -239.7 |
| 2 | 472 | 184 | -288 | -156.5 |
| 3 | 645 | 394 | -251 | -63.7 |
| 4 | 891 | 611 | -280 | -45.8 |
| 5 | 292 | 133 | -159 | -119.5 |

# DETECTION SYSTEM FOR FLOW CONTROL APPARATUS

CROSS-REFERENCE TO RELATED APPLICATIONS

This application claims priority to U.S. Provisional Patent Application No. 63/028,951 filed on May 22, 2020, the contents of which are incorporated by reference herein in their entirety.

TECHNICAL FIELD

The present disclosure generally relates to a flow control apparatus capable of detecting a condition of a pump set mounted on the apparatus.

BACKGROUND

Administering fluids containing medicine or nutrition to a patient is generally well known in the art. Typically, fluid is delivered to the patient by a pump set received by a flow control apparatus, such as a pump, connected to a source of fluid which delivers fluid to a patient. A flow control apparatus of the prior art may also be capable of monitoring and detecting fluid flow conditions that can occur within the loaded administration feeding set during operation of the flow control apparatus. Generally, prior art flow monitoring systems that are capable of monitoring and detecting flow conditions may rely on sensors arranged relative to the administration feeding set.

SUMMARY

The following presents a simplified summary of one or more implementations of the present disclosure in order to provide a basic understanding of such implementations. This summary is not an extensive overview of all contemplated implementations, and is intended to neither identify key or critical elements of all implementations nor delineate the scope of any or all implementations. Its sole purpose is to present some concepts of one or more implementations of the present disclosure in a simplified form as a prelude to the more detailed description that is presented later.

In one aspect, the disclosure provides a system, method and non-transitory computer readable medium storing computer executable instructions that may be executed by a processor for detecting the flow of a fluid via a control apparatus. The system, method and non-transitory computer readable medium may include a housing capable of receiving a portion of the feeding set. The system, method and non-transitory computer readable medium may also include a pumping device associated with the housing and positioned to engage the feeding set when the feeding set is received by the housing so the pumping device engages the feeding set to produce fluid flow in the feeding set to deliver fluid to a subject. The system, method and non-transitory computer readable medium may also include an ultrasonic sensor arranged with respect to the pumping device to produce a sensor signal indicative of a condition of the feeding set, where the ultrasonic sensor may comprise a plurality of sensor components such that the ultrasonic sensor is configured to emit an ultrasonic signal in a first direction from one of the plurality of sensor components though the feeding set, and in a second direction opposite the first direction from another of the plurality of sensor components through the feeding set. The system, method and non-transitory computer readable medium may also include a control circuit in communication with the ultrasonic sensor for receiving the sensor signal from the ultrasonic sensor indicative of the condition of the feeding set.

In one aspect, the disclosure provides a system, method and non-transitory computer readable medium storing computer executable instructions that may be executed by a processor for detecting the flow of a fluid via a control apparatus. The system, method and non-transitory computer readable medium may include emitting a first ultrasonic signal in a first direction though a portion of a pump set. The system, method and non-transitory computer readable medium may also include emitting a second ultrasonic signal in a second direction though the portion of a pump set, the second direction being opposite the first direction. The system, method and non-transitory computer readable medium may also include detecting the first ultrasonic signal to determine a first sensor reading. The system, method and non-transitory computer readable medium may also include detecting the second ultrasonic signal to determine a second sensor reading. The system, method and non-transitory computer readable medium may also include comparing an amplitude of the first sensor reading to an amplitude of the second sensor reading. The system, method and non-transitory computer readable medium may also include detecting a condition of the pump set based on the comparing of the first sensor reading and the second sensor reading.

In one aspect, the disclosure provides a system, method and non-transitory computer readable medium storing computer executable instructions that may be executed by a processor for detecting the flow of a fluid via a control apparatus. The system, method and non-transitory computer readable medium may include emitting via a first sensor component a first ultrasonic signal in a first direction though a portion of a pump set. emitting via a second sensor component a second ultrasonic signal in a second direction though the portion of a pump set, the second direction being opposite the first direction. The system, method and non-transitory computer readable medium may also include detecting the first ultrasonic signal to determine a first sensor reading. The system, method and non-transitory computer readable medium may also include detecting the second ultrasonic signal to determine a second sensor reading. The system, method and non-transitory computer readable medium may also include comparing an amplitude of the first sensor reading to an amplitude of the second sensor reading. The system, method and non-transitory computer readable medium may also include detecting a condition of the pump set based on the comparing of the first sensor reading and the second sensor reading.

In one aspect, the disclosure provides a system, method and non-transitory computer readable medium storing computer executable instructions that may be executed by a processor for detecting the flow of a fluid via a control apparatus. The system, method and non-transitory computer readable medium may include a housing configured to receive a feeding set. The system, method and non-transitory computer readable medium may also include a pumping device configured to produce a fluid flow in the feeding set. The system, method and non-transitory computer readable medium may also include an ultrasonic sensor including a first sensor component and a second sensor component, the first sensor component configured to emit a first ultrasonic signal though a portion of the feeding set in a first direction and the second sensor component configured to emit a second ultrasonic signal though the portion of the feeding set in a second direction. The system, method and non-transitory computer readable medium may also include a control circuit configured to switch between a first configuration and a second configuration, whereby the first configuration includes the first sensor component emits the first ultrasonic signal directed to the second sensor component for detection by the second sensor component, and wherein the second configuration includes the second sensor component emits the second ultrasonic signal directed to the first sensor component for detection by the first sensor component.

In one aspect, the disclosure provides a system, method and non-transitory computer readable medium storing computer executable instructions that may be executed by a processor for detecting the flow of a fluid via a control apparatus. The system, method and non-transitory computer readable medium may include a housing configured to receive a feeding set. The system, method and non-transitory computer readable medium may also include a pumping device configured to produce a fluid flow in the feeding set. The system, method and non-transitory computer readable medium may also include a first ultrasonic sensor configured to produce a first sensor signal indicative of a first condition of a first portion of the feeding set. The system, method and non-transitory computer readable medium may also include a second ultrasonic sensor configured to produce a second sensor signal indicative of a first condition of a second portion of the feeding set. The system, method and non-transitory computer readable medium may also include a pressure sensor configured to produce a pressure signal indicative of a third condition of the feeding set. The system, method and non-transitory computer readable medium may also include a control circuit in communication with the first ultrasonic sensor, the second ultrasonic sensor and the pressure sensor and configured to receive the first sensor signal, the second sensor signal and the pressure signal, wherein the control circuit is configured to provide an initial indication that fluid is present in the feeding set based upon the first sensor signal or the second sensor signal, or provide an initial indication of an occlusion in the feeding set based on the pressure signal.

In one aspect, the disclosure provides a system, method and non-transitory computer readable medium storing computer executable instructions that may be executed by a processor for detecting the flow of a fluid via a control apparatus. The system, method and non-transitory computer readable medium may include generating a first sensor signal indicative of a first condition of a first portion of a feeding set. The system, method and non-transitory computer readable medium may also include generating a second sensor signal indicative of a first condition of a second portion of the feeding set. The system, method and non-transitory computer readable medium may also include generating a pressure signal indicative of a third condition of the feeding set. The system, method and non-transitory computer readable medium may also include receiving the first sensor signal, the second sensor signal and the pressure signal. The system, method and non-transitory computer readable medium may also include generating an initial indication that fluid is present in the feeding set based upon the first sensor signal or the second sensor signal, or provide an initial indication of an occlusion in the feeding set based on the pressure signal.

Additional advantages and novel features relating to implementations of the present disclosure will be set forth in part in the description that follows, and in part will become more apparent to those skilled in the art upon examination of the following or upon learning by practice thereof.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objects and advances thereof, will be best understood by reference to the following detailed description of illustrative aspects of the disclosure when read in conjunction with the accompanying drawings, wherein:

FIG. 11 is a flowchart of an example method of a fluid detection routine in accordance with an implementation of the present disclosure;

FIG. 12 is a flowchart of an example method of an occlusion detection routine in accordance with an implementation of the present disclosure;

FIG. 13A, FIG. 13B and FIG. 13C illustrate example results associated with the example illustrations of the skewed tubing received within a sensor track in accordance with FIG. 6A and FIG. 6B;

DETAILED DESCRIPTION

Figure 1:
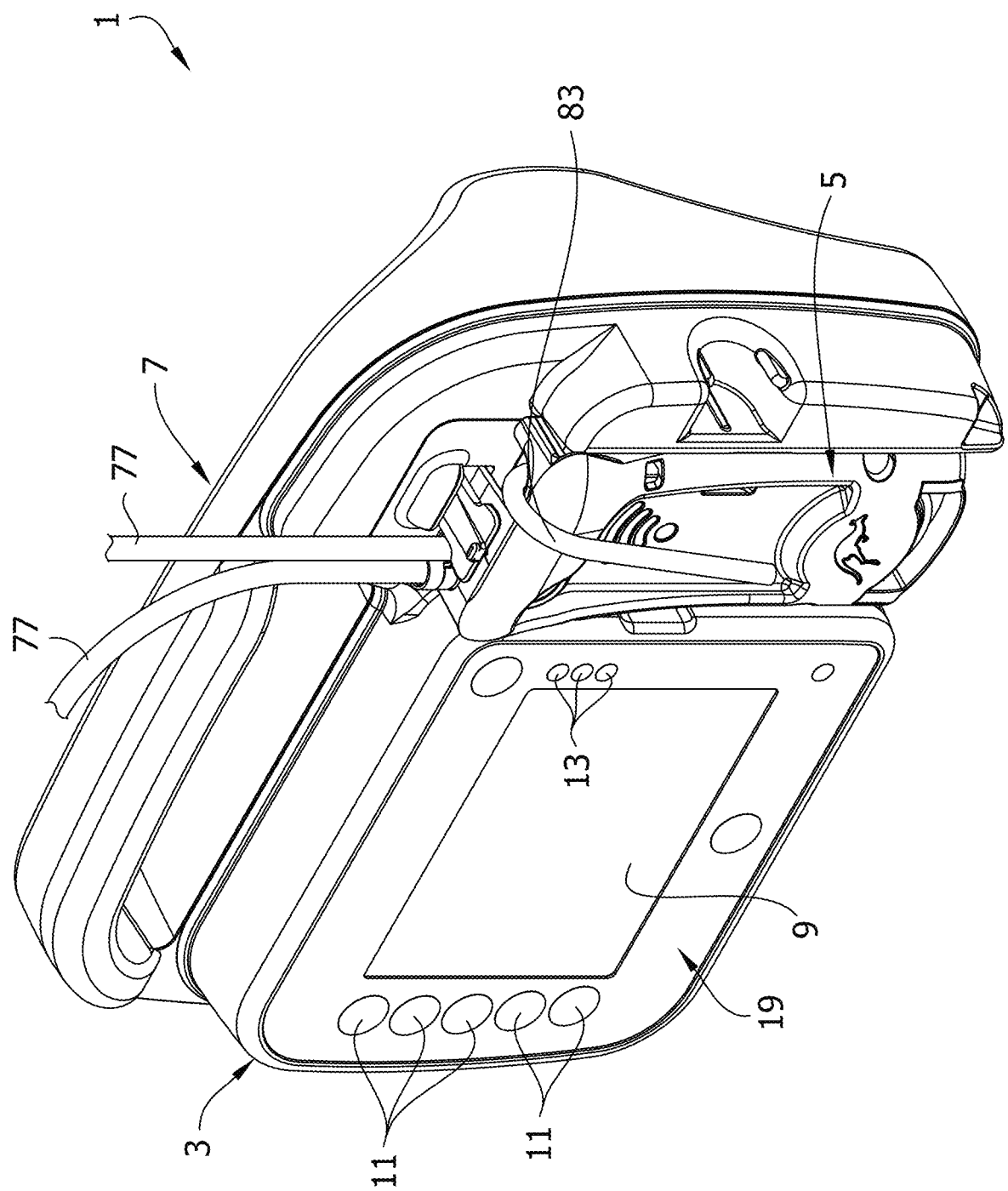
FIG. 1 is a perspective view of an example enteral feeding pump and a fragmentary portion of a feeding set received on the pump in accordance with aspects of the present disclosure.

Referring now to the example aspects schematically illustrated in FIGS. 1-3, an enteral feeding pump (broadly, "a flow control apparatus") and hereinafter interchangeably referred to throughout this disclosure as a "pump" is generally indicated at 1. The pump 1 may comprise a housing 3 constructed so as to mount a cassette, generally indicated at 5, and a feeding set (broadly, a "pump set"), a fragmentary portion generally indicated at 7, removably received in the cassette. The feeding set 7 can comprise tubing indicated generally at 77 that provides a fluidic pathway between a source of nutritional liquid and a flushing liquid (FIG. 1). Tubing 83 provide a fluidic pathway from the pump 1 to a user. In aspects of the disclosure the end user may be one of a patient or administrator of the enteral feeding pump. As will be explained in greater detail below, the pump 1 may comprise a flow monitoring system 6 (FIG. 4) that is capable of detecting and identifying a condition of the feeding set 7 loaded on the pump. As used herein, the term "load" means that the feeding set 7 is engaged with the pump 1 so that the feeding set is ready for operation with the pump to deliver fluid to the patient.

Figure 3:
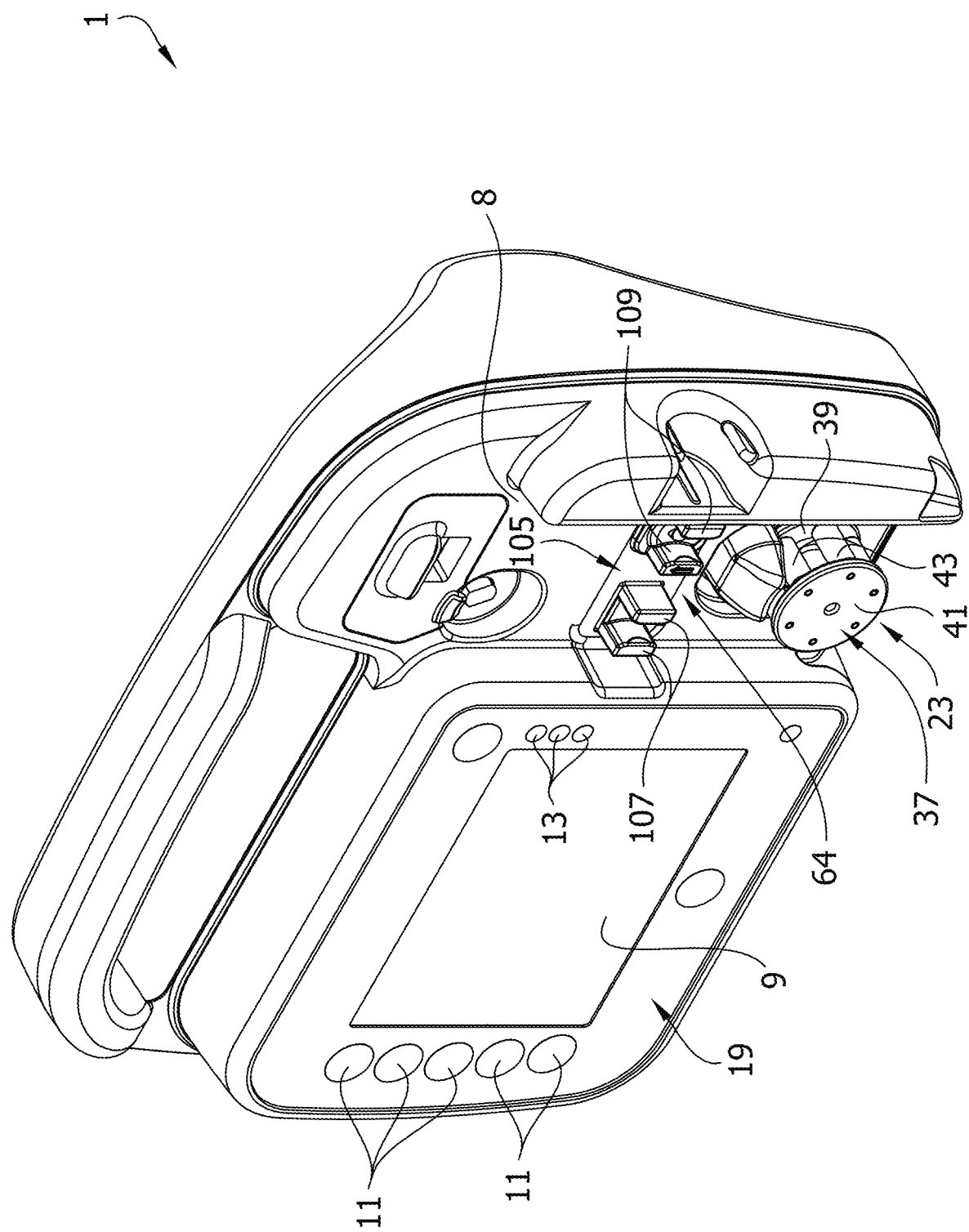
FIG. 3 is the perspective view of FIG. 2 with the feeding set removed.

In the illustrated aspects, the cassette 5 is removably received in a cassette recess 8 in the housing 3 (FIG. 3). It will be appreciated that "housing" as used herein may include many forms of supporting structures (not shown), including without limitation multi-part structures and structures that do not enclose or house the working components of the pump 1. Moreover, various aspects and features of the present disclosure can be implemented without the recess 8. The pump 1 may also comprise a display screen 9 on the housing 3 that is capable of displaying information pertaining to the status and operation of the pump. One or more buttons 11 which can be proximate the display screen 9 can be provided for use in controlling and obtaining information from the pump 1, and one or more light emitting devices ("LEDs") 13 can provide status information for the pump. In one aspect of the disclosure the light emitting devices may be any form of a device which emitted lights, for example, fiber optics, light emitting diodes, and the like. For example, the LEDs 13 may indicate proper or improper functionality of the pump 1. Additionally, for example, the LEDs may also indicate when fluid is properly or improperly flowing or not flowing through the feeding set 7. Legs (not shown) may be disposed at the bottom of the housing 3 to support the housing so that the display screen 9 is angled slightly upward for ease of viewing by a user.

The display screen 9 may be part of a front panel (generally indicated at 19) of the housing 3 and may be removably attached to the housing. The pump 1 may further include a pumping unit indicated generally at 23 comprising a pump motor 27 (FIG. 4) connected to a rotor shaft. A battery (not shown) may be received in the housing 3 for powering the pump motor. A power source other than or in addition to the battery could be used to energize the pump including one or more prime movers which drive the pumping unit through the rotor shaft. Another example of a pump with a rotor shaft is disclosed in U.S. Patent Publication No. 2020/0352827, the entire disclosure of which is herein incorporated by reference.

The pumping unit 23 can have a rotor (generally indicated at 37) which can be coupled to the rotor shaft. The rotor 37 may include an inner disk 39, an outer disk 41, and rollers 43 (preferably four, but only two of which are indicated). Inner disk 39 and outer disk 41 preferably lie in parallel planes, spaced from one another and rotatable about a shared axis. Rollers 43 are mounted between the inner disk 39 and the outer disk 41 for planetary rotation about the shared axis of the disks 39, 41. Each roller 43 is also mounted to the disks 39, 41 for rotation relative to the disks 39, 41 about its own longitudinal axis (FIGS. 2 and 3), which may be parallel to the shared axis of the disks 39, 41. As the rollers 43 rotate about the axis of the disks 39, 41, they engage a tube 45 (FIG. 2) of the feeding set 7 to deliver fluid through the feeding set, via peristaltic engagement, to a patient when the feeding set is received in the cassette 5 and the cassette is attached to the housing 3. Other numbers of rollers may also be envisioned and implemented. For example and without limitation, five or six rollers may also be used without departing from the scope of the disclosure.

The rollers 43 may engage the feeding set 7 for moving fluid through the feeding set. In the illustrated aspect, the pump motor 27, rotor shaft, and rotor 37, may broadly be considered "a pumping device." These components may be individually considered "a pumping device." It will be understood that peristaltic pumps that use mechanisms other than rollers may fall within the scope of the present disclosure. However, other pumping devices (e.g., non-rotary devices) are envisioned.

As used herein, the portion of tubing 77 of the feeding set 7 leading to the rotor 37 is termed "upstream," while the tubing 83 leading away from the rotor 37 to the patient is termed "downstream." Rotation of the rotor 37 compresses the tube 45 of the feeding set 7 to drive fluid (e.g., a nutritional liquid) in a patient direction from the upstream to the downstream side of the feeding set. Although an example feeding set 7 is shown, feeding sets of other configurations and other types of pump sets (not shown) can be used.

Figure 2:
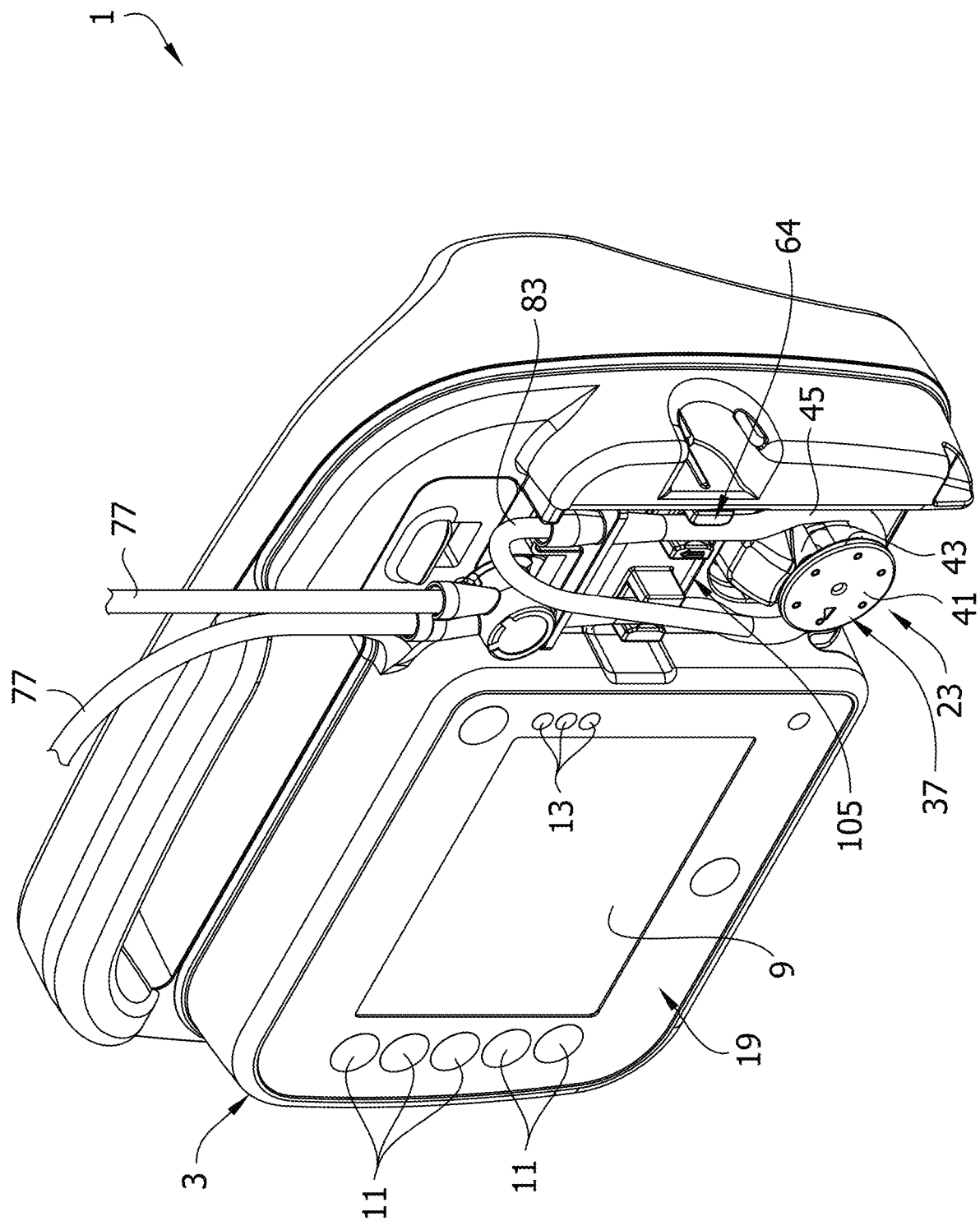
FIG. 2 is a perspective view of FIG. 1 with a cassette housing of the feeding set removed.
Figure 4:
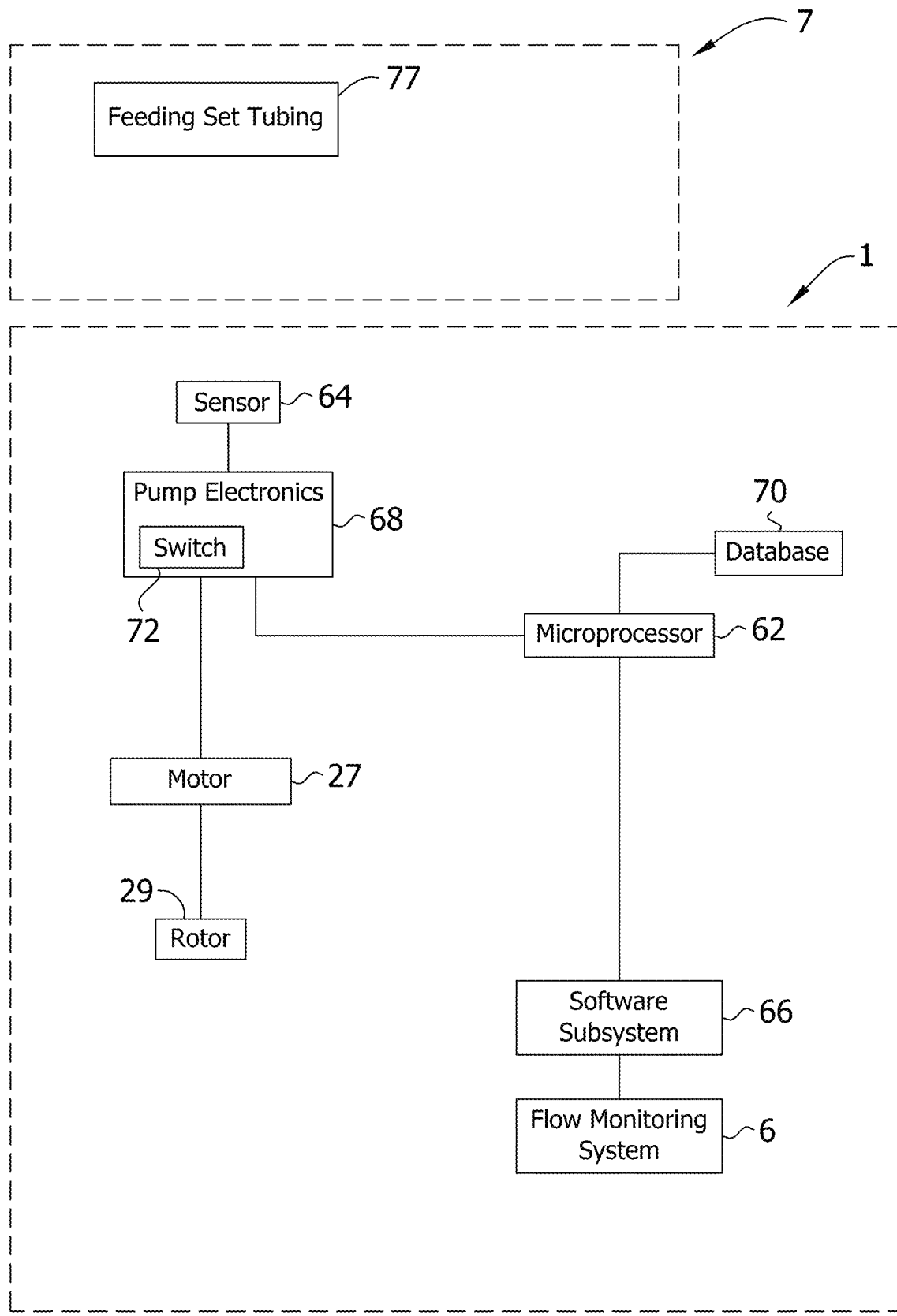
FIG. 4 is a block diagram illustrating elements of an example enteral feeding pump including a flow monitoring system in accordance with aspects of the present disclosure.

Referring to FIG. 2-4, the monitoring system 6 (FIG. 4) is capable of detecting and identifying a condition of the feeding set 7 loaded on the apparatus. For example, a condition of the feeding set 7 may relate to the flow of liquid through the set, whether the set is mounted properly on the pump, whether there is an occlusion, or other circumstances pertaining to the feeding set or its operation. For example, the flow of liquid through the set may include the lack of or improper flow of liquid through the set. Additionally, for example, if the set is improperly mounted on the pump, fluid may not flow properly through the set. Additionally, for example, when the set is improperly mounted on the pump an occlusion may be present within the tubing.

The pump 1 may further comprise a microprocessor 62 in communication association with a sensor 64. The microprocessor 62 may control and manage the operation of the various components of the pump 1. A software subsystem 66 may be operatively associated with the microprocessor 62 and operatively associated with the monitoring system 6 to provide a means for the pump 1 to detect and identify a condition of the feeding set 7. It is to be understood that in the described aspect, the flow monitoring system 6, the software subsystem 66, pump electronics 68, the microprocessor 62 and memory 70 may be broadly considered a "control circuit." These components may be individually considered a "control circuit." Moreover, other types of control circuits may be used within the scope of the present disclosure. As described in reference to FIGS. 15 and 16 below, the control circuit may be implemented in relation to the various components.

The sensor 64 may comprise one or more ultrasonic sensors. The sensor 64 may be located on the housing 3 of the pump 1 and positioned to detect the presence of fluid as well as one or more properties of a fluid in the feeding set 7, e.g., an occlusion of the fluid in the feeding set. In the illustrated aspect, the sensor 64 is positioned in recess 8 and is adapted to securely receive a portion of the tube 45 therein when the feeding set 7 is loaded on the pump 1. In order for the sensor 64 to detect the presence of fluid in the tube 45 of the feeding set 7, the tube may be engaged and retained within a sensor track 105 (FIG. 3) configured to receive an upstream portion and a downstream portion of the tube 45. Once the tube 45 is engaged within the sensor track 105 and the remaining portions of the feeding set 7 are engaged with the pump 1, the monitoring system 6 may become operational. For example, the monitoring system 6 may become operationally functional when a positive engagement of the tube 45 within the sensor track 105 has been identified by the receipt of an acceptable signal, e.g., an ultrasonic signal, by one or more detectors or receivers. The sensor 64 may be positioned perpendicular to the direction of the feeding set 7. For example the sensor 64 may be positioned to read horizontally, while the feeding set 7 may be positioned to flow fluid vertically. In one aspect of the disclosure, the sensor 64 is set at a 90 degree angle in relation to the feeding set 7. As described in more detail below, although an attempt may be made to position the sensor 64 to read the tube 45 of the feeding set 7 engaged in the sensor track 105 horizontally, the tube 45 or the sensor 64 may be misaligned thereby providing less than ideal readings. The sensor may output erroneous indications, for example, indicating a wrong condition, as described above.

In one aspect of the disclosure, the sensor 64 may comprise a first sensor component 107, 109 for transmitting an ultrasonic signal through an upstream and downstream portion of the tube 45, respectively, and a second sensor component 107, 109 configured to receive and detect the ultrasonic signal emitted from the first sensor component. Upon receipt of the ultrasonic signal from the first sensor component 107, 109, the second sensor component 107, 109 may detect the presence of fluid within the tube 45 based on the characteristics of the ultrasonic signal received by the second sensor component and communicated to the microprocessor 62. The first and second sensor components 107, 109 may each comprise identical or substantially identical sensor configurations. For example, each sensor component 107, 109 may comprise ultrasonic crystals whereby each sensor component can be operated as a transmitter for transmitting the ultrasonic signal, or as a detector for detecting the ultrasonic signal depending on the way in which the components are energized. Therefore, the direction of the ultrasonic signal is not confined to a single direction between the sensor components 107, 109 but instead can be directed in both directions between the sensor components.

The sensor 64 may detect the presence or absence of fluid in the tubing to give a basic indication of the operational status of the pump 1. The ultrasonic signal emitted from the sensor components 107, 109 may be responsive to the presence of fluid in the tube 45 such that fluid in the tube will produce an increase in amplitude of the signal as compared to a signal where fluid is not in the tubing. As such, an ultrasonic signal passing through an all air media will not produce a signal at the detector. Based on the characteristics of the received ultrasonic signal communicated to the microprocessor 62, the software subsystem 66 may determine whether fluid is present within the feeding set 7. Other types of sensors for measuring one or more fluid properties or characteristics, including viscosity, other than ultrasonic sensors can be used. The flow monitoring system 6 may also detect other conditions of the feeding set 7, the fluid within the feeding set, and the fluid coupled with the feeding set without departing from the scope of the disclosure.

Figure 5A:
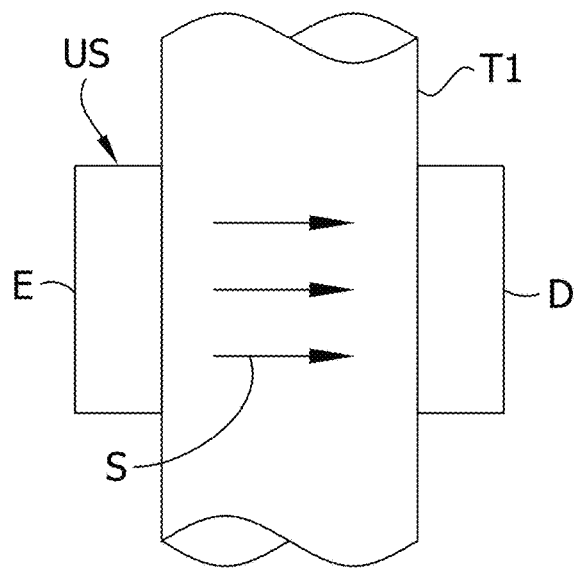
FIGS. 5A-5C are example illustrations of tubing received in a sensor track in accordance with aspects of the present disclosure.
Figure 5B:
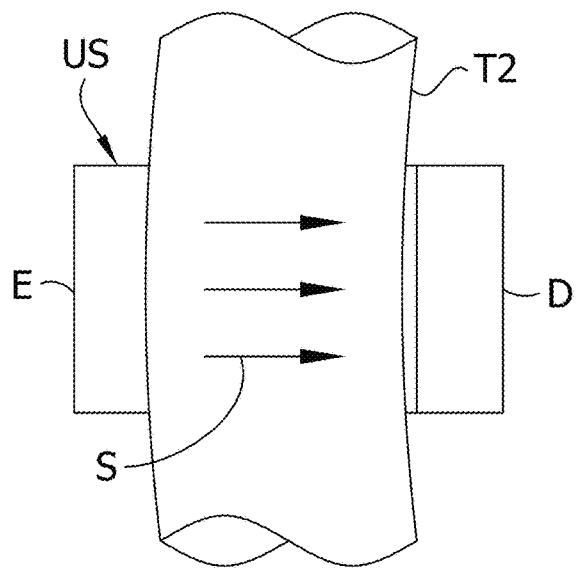
Figure 5C:
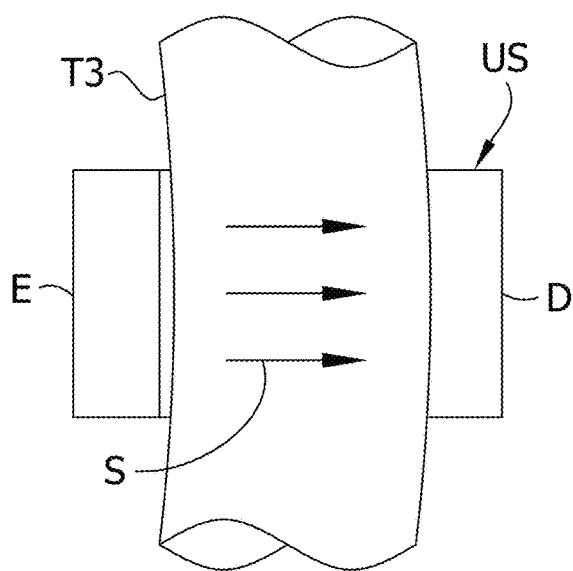

Referring to FIGS. 5A-5C, errors and inaccurate readings may arise with the signal strength of an ultrasonic sensor "US" when the tubing is skewed within the sensor track 105 of FIG. 3. In one aspect of the disclosure, tube T1 should be positioned at a substantially vertical orientation within the sensor track 105 of FIG. 3 such that the tubing spans an entire width between the sensor components E, D of the sensor US (FIG. 5A). Sensor components E and D are considered the emitter and detector, respectively. In this instance, the ultrasonic signal S does not pass through air prior to or after passing through the tube T1. Thus, the sensor reading generated by the sensor US produces an expected output reading/result based on whether fluid is or is not present within the tube T1. In this aspect of the disclosure, the assumes that the sensor US is performing correctly. In other words, the sensor US is built and manufactured without gaps or air on either side or inside of E and D of the sensor US. If gaps or air pockets are present within either side or inside E or D, the sensor US may still obtain erroneous or inaccurate readings regarding whether fluid is or is not present even if the tube T1 is positioned at a substantially vertical origination within the sensor track 105 of FIG. 3. In another aspect of the disclosure described in more detail below, the gaps or air pockets introducing errors within the readings may compensated for in order to correct or adjust the errors and inaccurate readings.

In another aspect of the disclosure, when the tubing T2 and/or T3 is skewed toward either sensor component E or D, the sensor US reading may be inaccurate, for example, higher or lower than expected which can result in a false reading. In particular, if the tube T2 is skewed toward an emitter side E of the sensor US (FIG. 5B), the signal received at the detector D will be stronger than if the tubing T3 is skewed toward the detector side D of the sensor (FIG. 5C). As a result, for example, when the tubing T3 is skewed toward the detector side D of the sensor US, a sensor reading may indicate that no fluid is present within the tubing (i.e., low signal) when fluid is actually present in the tubing. For example, when the tubing T3 is skewed toward the detector side D, a reading of X by the sensor US may be determined. The reading of X may then be compared to a threshold Y. When the reading X is lower than the threshold Y, the pump may determine that no fluid is present within the tube T3 and alert a user, as described below, when fluid is actually present. This may provide false and erroneous readings and outputs which cost time, money and loss of confidence to a user. In another aspect of the disclosure, for example, when the tubing T2 is skewed toward the emitter side E of the sensor US, a sensor reading may indicate that fluid is present within the tubing (i.e., high signal). For example, when the tubing T2 is skewed toward the emitter side E, a reading of X by the sensor US may be determined. The reading of X may then be compared to a threshold Y. When the reading X is higher than the threshold Y, the pump may determine that fluid is present within the tube T2. This approach may provide fewer false and erroneous readings and outputs which cost time, money and loss of confidence to a user.

Figure 6A:
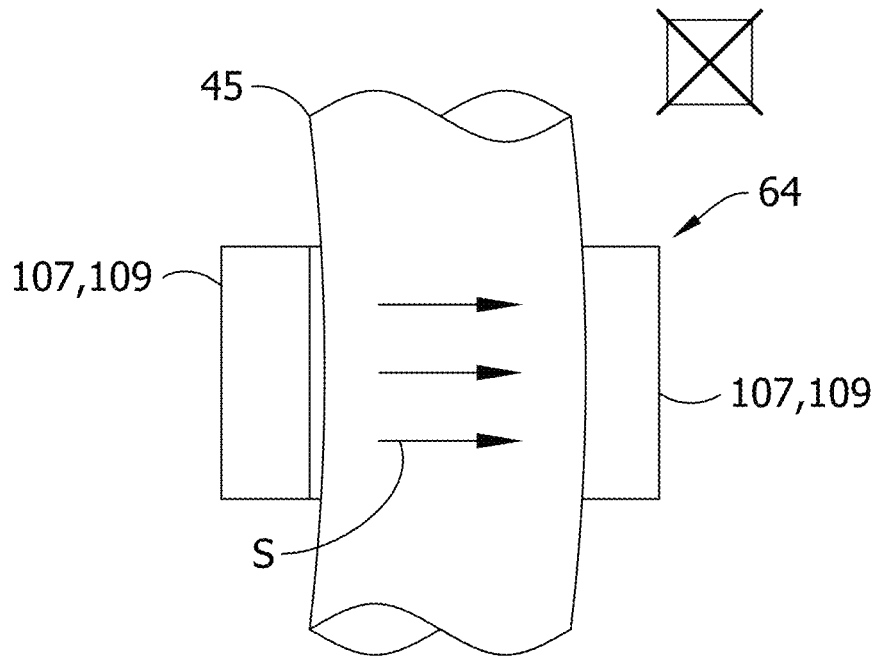
FIGS. 6A-6B are example illustrations of a skewed tubing received within a sensor track in accordance with aspects of the present disclosure.
Figure 6B:
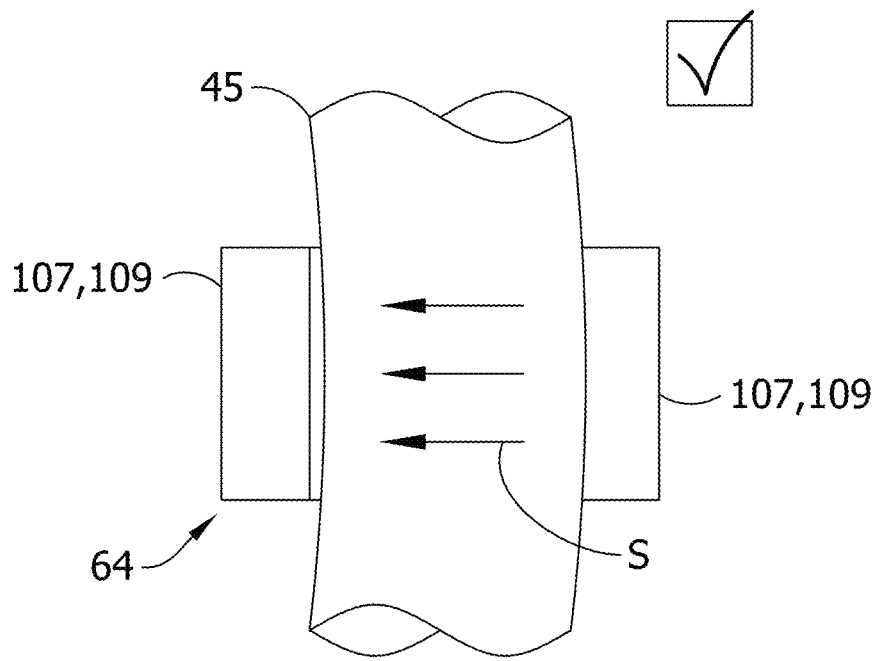

Referring to FIGS. 4, 6A, and 6B, included within the pump electronics 68 are one or more switches 72 configured to control which sensor component 107, 109 operates as the emitter E for emitting the ultrasonic signal S and which sensor component operates as the detector D for receiving and detecting the ultrasonic signal. Therefore, the pump 1 is configured to adapt to the orientation and/or dimensions of the tube 45 of the pump set 7 to optimize the performance of the sensor 64. The one or more switches 72 are electrically connected to the sensor 64 for reconfiguring the electrical circuit to selectively energize one of the sensor components 107, 109 to configure the energized component as the ultrasonic emitter E. Thus, depending on the position of the tube 45 in the sensor track 105, the pump 1 can select which sensor component 107, 109 to operate as the emitter E and which sensor component to operate as the detector D to maximize the signal strength. For example, as described in reference to FIGS. 13A, 13B and 13C below, the pump 1 can acquire two different readings on a single tube orientation based upon switching the sensor components 107, 109 between operation as an emitter E or detector D to determine a higher sensor US reading. As a result, the pump 1 addresses the issues that can arise with conventional pumps when the emitter and detector are preset and the position or orientation of the tubing alters (e.g., reduces) the expected sensor reading in certain circumstances (FIG. 5C). For instance, the tube 45 may be configured such that the tube is skewed within the sensor track 105 in the direction shown in FIG. 6A. If the pump electronics 68 are set such that the left sensor components 107, 109 operates as the emitter and the right sensor component 107, 109 operates as the detector, then the sensor signal S will be lower than the expected signal strength for a given fluid condition particularly if the pump 1 is calibrated to assume that the tube 45 is positioned substantially vertically across the sensor path. However, to account for this potential misalignment of the tube 45, the pump 1 may activate one of the one or more switches 72 to energize the right sensor component 107, 109 such that it operates as the emitter and the left sensor component operates as the detector (FIG. 6B). As a result, the signal strength of the ultrasonic signal S will be increased and will more closely approximate the ideal conditions where the tube is oriented vertically. Thus, the condition is alleviated where a low signal could incorrectly indicate that no fluid is present in the tube 45 when there is in fact fluid in the tube. As a result, feeding tubes of various conditions can be utilized without compromising the accuracy of the feeding set detections. Moreover, the need to squish or flatten the tube to obtain a better fit within the sensor track is alleviated. Thus, this processing set which can impair the integrity of the tubing is removed.

Additionally, in accordance with another aspect of the disclosure, the pump 1 addresses issues that can arise with conventional pumps when the sensor US contains flaws (gaps, air pockets, and the like) which are present within the emitter or detector that are created during the manufacturing process. As described above, although more accurate readings are usually acquired when the tube is skewed towards the emitter E, flaws may be present with sensor component 107, 109, such as air pockets and/or gaps which would provide for erroneous readings of signal S. For example, in reference to FIG. 6B, if the pump electronics 68 are set such that the left sensor components 107, 109 operate as the emitter and the right sensor components 107, 109 operate as the detector, then the sensor signal S should be expected to be lower than the expected signal strength for a given fluid condition, particularly if the pump 1 is calibrated to assume that the tube 45 is positioned substantially vertically across the sensor path. However, as described above, to account for this potential misalignment of the tube 45, the pump 1 may activate one of the one or more switches 72 to energize the right sensor components 107, 109 such that it operates as the emitter and the left sensor component operates as the detector (FIG. 6B). As a result, the signal strength of the ultrasonic signal S would be expected to be increased and more closely approximate the ideal conditions where the tube is oriented vertically. In one aspect of the disclosure, the manufacturing process presented flaws within the right sensor components 107, 109 and thereby injected large errors within the signal S which provides for lower results than expect. Thus, although normally the results of a tube skewed closer to the emitter E would provide for higher and more accurate results regarding fluid flow, in this example, the system provides higher and more accurate results from the reading when the left sensor components 107, 109 operate as the emitter and the right sensor components 107, 109 operate as the detector based on the flaws of the left sensor components 107, 109. Through this process, the pump 1 selects the reading with the highest results regardless of the tube orientation and operation/configuration of the sensor components 107, 109. As a result, feeding tubes of various conditions, sensor components with various flaws can be utilized without compromising the accuracy of the feeding set detections. Moreover, the need to compress or flatten the tube to obtain a better fit within the sensor track is alleviated. Thus, this processing set which can impair the integrity of the tubing is removed. Moreover, the need to test for quality control the sensor US to obtain exact results is alleviated.

Figure 7:
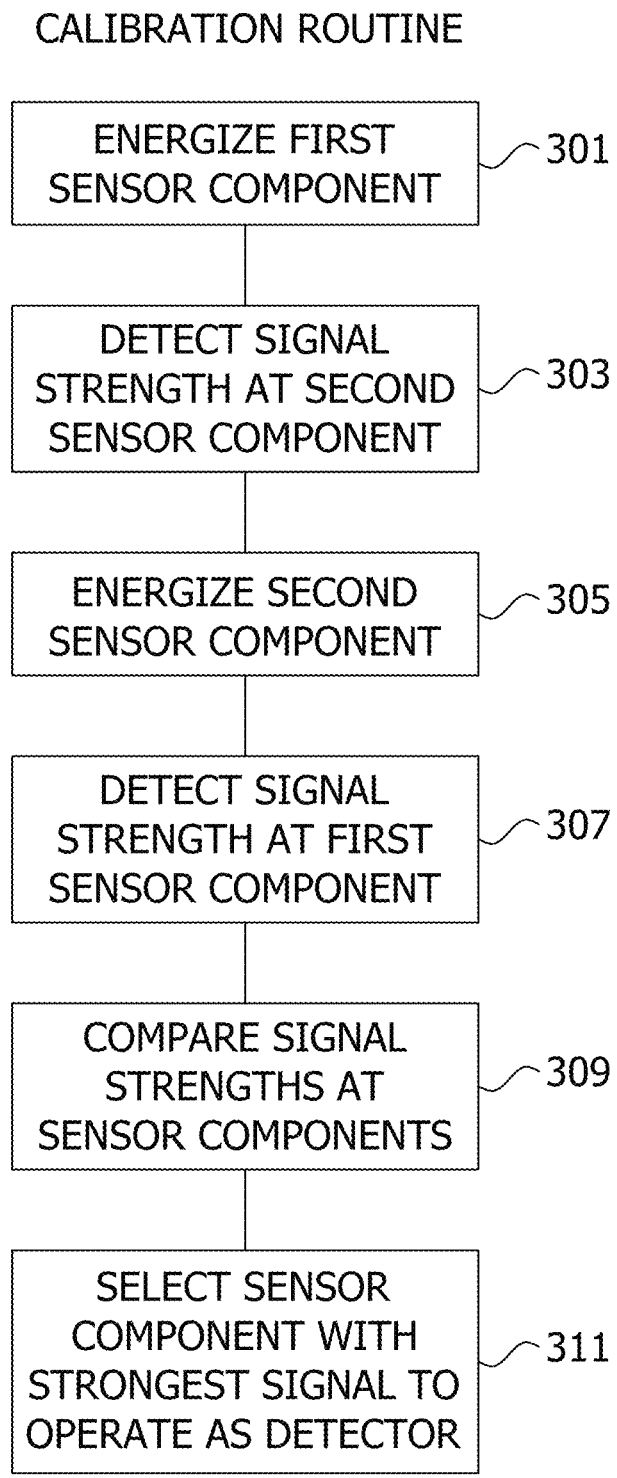
FIG. 7 is a flowchart of an example calibration method in accordance with aspects of the present disclosure.

In another aspect of the disclosure, operation of the pump 1 may be such that a sensor calibration routine is automatically performed (for example, each power cycle or when a new cassette is connected) or initiated in response to a user activated command to calibrate the sensor 64 to accommodate for the position/orientation of the tube 45. For example, and with reference to FIG. 7, the sensor calibration routine may be initiated after the pump 1 confirms that the feeding set 7 has been loaded onto the pump and/or at the start of each feeding cycle. Still other actions to initiate the calibration routine are envisioned. At a first step 301, a first sensor component 107, 109 is energized to emit an ultrasonic signal toward a second sensor component 107, 109 opposite the first sensor component. At 303, a strength of the signal detected by the second sensor component is measured and stored in the memory 70. At 305, the second sensor component 107, 109 is energized to emit an ultrasonic signal toward the first sensor component. The strength of the signal detected by the first sensor component 107, 109 is then measured and stored in the memory 70, at 307. The strength of the signal at the second sensor component 107, 109 is then compared to the strength of the signal at the first sensor component 107, 109, at 309. At 311, the sensor component 107, 109 with the strongest signal will be configured to operate as the detector in the sensor pair during operation of the pump 1 to deliver fluid though the tubing to the patient.

Figure 8:
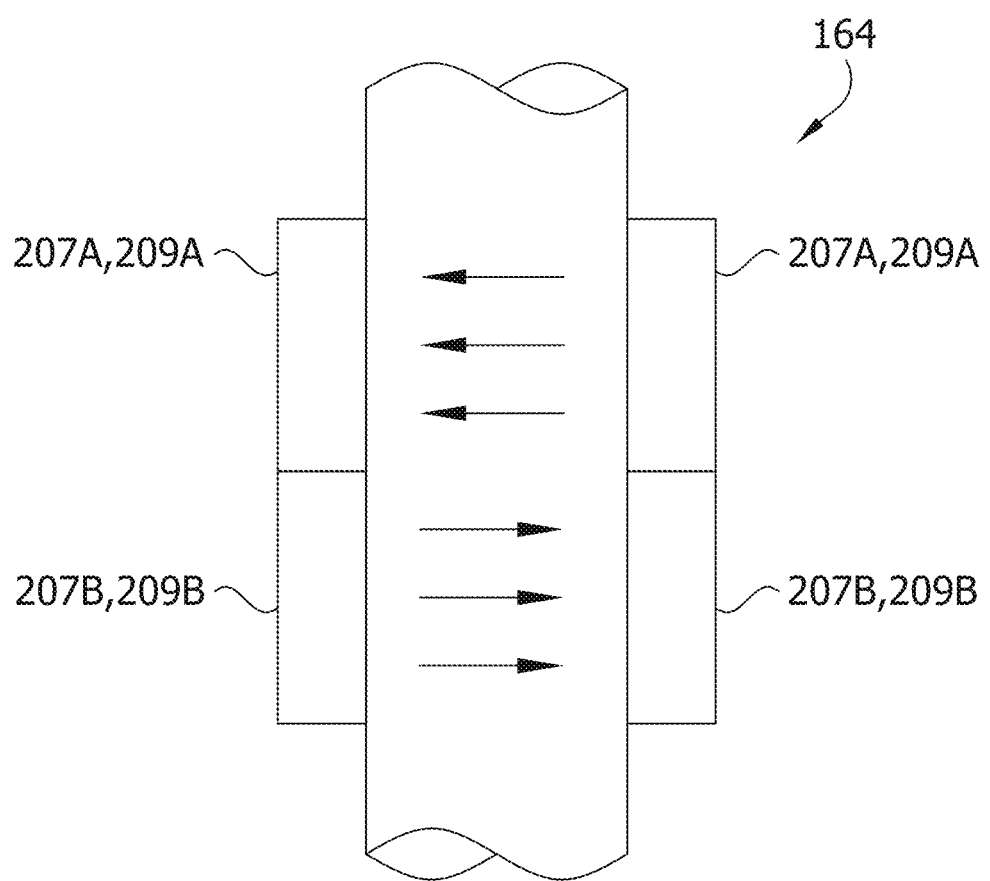
FIG. 8 is an example illustration of a tubing received within a sensor track in accordance with aspects of the present disclosure.

Referring to FIG. 8, in an ultrasonic sensor in accordance with another aspect of the disclosure, is generally indicated at 164. The sensor includes first and second pairs of sensor components 207A, 209A and 207B, 209B. Each sensor pair is configured identically to the sensor components 107, 109 described above. Additionally, the sensor pairs may be located at both/either the upstream side and/or downstream side of a sensor track for receiving upstream and downstream portions of a tube. A first (top) pair of sensor components 207A, 209A may be configured such that the right sensor component is operated as the emitter and the left sensor component is operated as the detector. A second (bottom) pair of sensor components 207B, 209B, may be configured such that the left sensor component is operated as the emitter and the right sensor component is operated as the detector. As such, a switch is not needed to switch emitter/ detector function between the sensor components. Instead, the pump can operate both pairs of sensor components 207A, 209A and 207B, 209B, respectively, and utilize the sensor readings from the sensor pair that produces the strongest signal at the detector side of the sensor pair in any determinations of the pump set. In accordance with an aspect of the disclosure, the strongest signal may be determined by comparing the sensor readings to a threshold and/or to each other. Additionally or alternatively, one or more switches can be operatively connected to the pairs of sensor components 207A, 209A and 207B, 209B, respectively, for switching emitter/detector functions between the sensor components of the sensor pairs.

Figure 9:
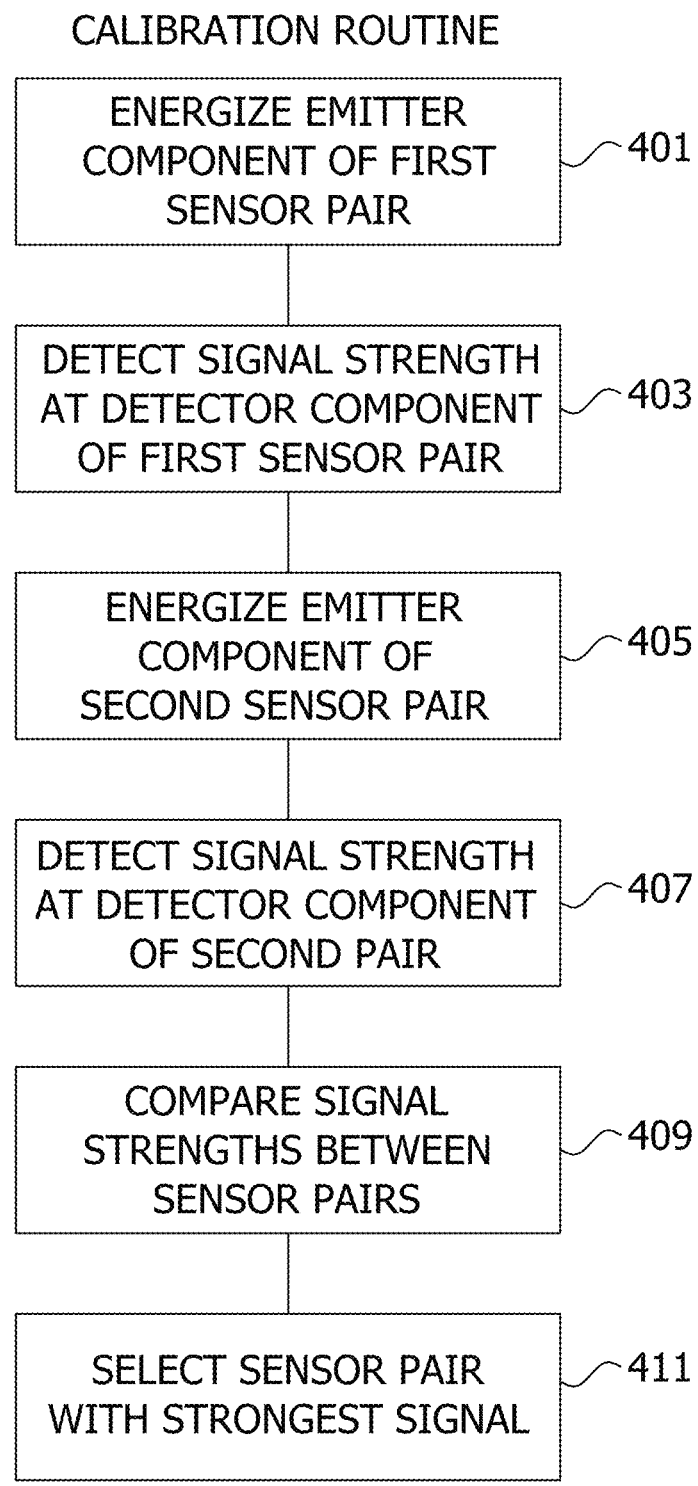
FIG. 9 is a flowchart of an example calibration method in accordance with an implementation of the present disclosure.

Referring to FIG. 9, a sensor calibration routine can also be performed with the sensor 164. At a first step 401, the sensor component 207A, 209A of the first sensor pair is energized to emit an ultrasonic signal toward the other sensor component 207A, 209A of that pair opposite the emitter component. At 403, a strength of the signal detected by the detector component is measured and stored in the pump memory. At 405, the sensor component 207B, 209B of the second sensor pair is energized to emit an ultrasonic signal toward the other sensor component 207B, 209B of that pair opposite the emitter component. The strength of the signal detected by the detector component of the second pair of sensor components 207B, 209B is then measured and stored in the pump memory, at 407. The strength of the signal between the second pair of sensor components 207B, 209B is then compared to the strength of the signal between the first pair of sensor components 207A, 209A, at 409. The pair of sensor components 207A, 207B and 209A, 209B, respectively, with the strongest signal will be configured, at 411, to operate as the controlling sensor during operation of the pump to deliver fluid though the tubing to the patient. It will be understood that more than two pairs of sensors may be used.

Figure 10:
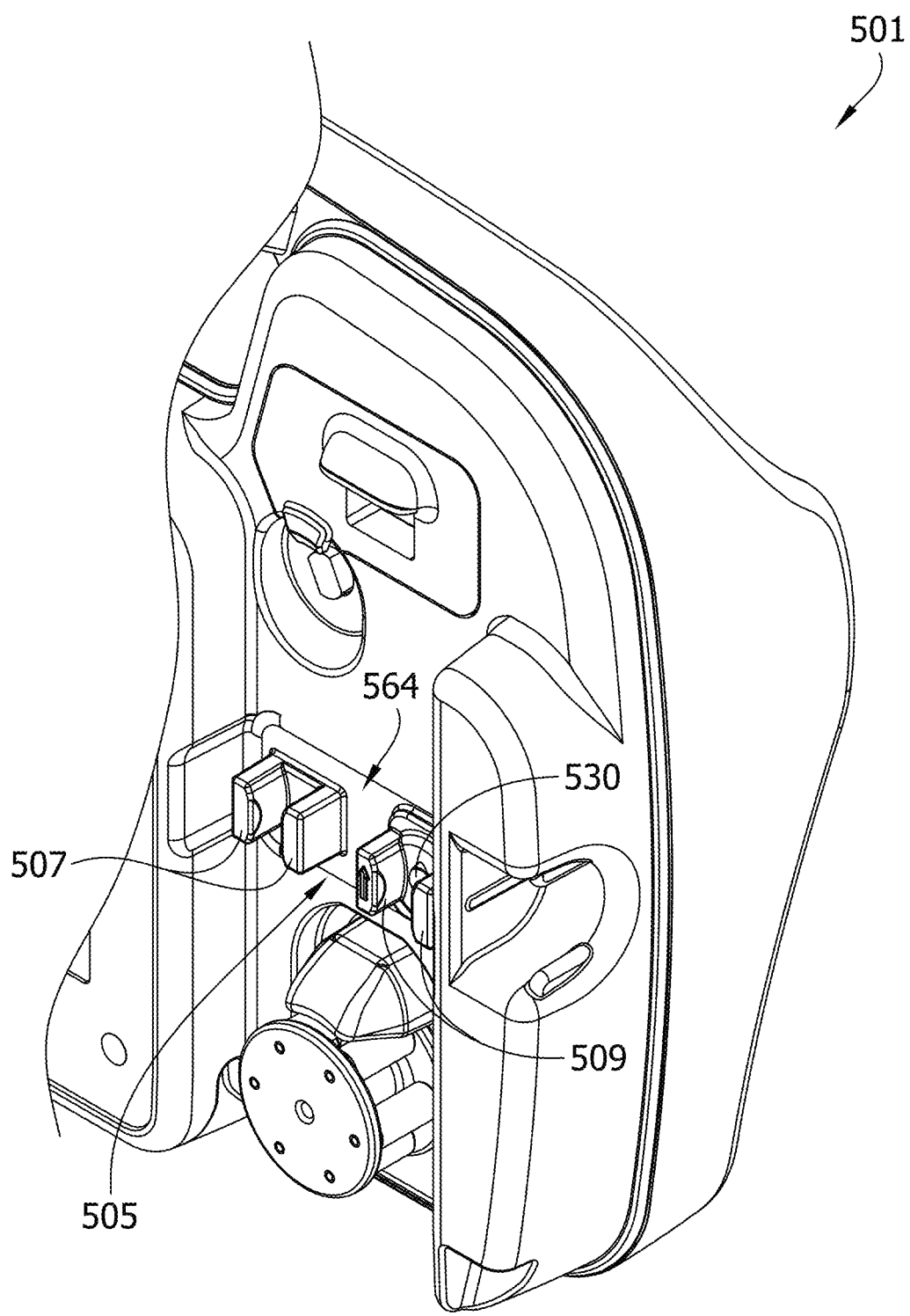
FIG. 10 is an enlarged, fragmentary perspective of an example enteral feeding pump in accordance with aspects of the present disclosure.

Referring to FIG. 10, a pump 501 of another aspect of the disclosure may comprise at least one ultrasonic sensor 564 including a first pair 507 of sensor components, a second pair 509 of sensor components and a pressure sensor 530 in combination with the ultrasonic sensor for detecting a force exerted by fluid flowing within the pump set. In one aspect, the pressure sensor 530 is located at the downstream side of the sensor track 505. In one aspect, the pressure sensor 530 is located at the upstream side of the sensor track 505. The pressure sensor 530 is configured to measure the expansion of tubing in the sensor track 505 in response to fluid flow in the tubing. For instance, fluid flow within the tubing may cause the tubing to expand a first amount and press against the pressure sensor 530, while an occlusion within the tubing may cause the tubing to expand an even greater amount as fluid pressure in the tubing increases. Thus, detecting a pressure above a first threshold may signal fluid flow within the tubing, and detecting a pressure above a second threshold, higher than the first threshold, may signal that an occlusion is present within the tubing. The pressure sensor 530 may also be configured to detect the presence of the feeding set separately from whether fluid is flowing through the feeding set. Thus, the pressure sensor 530 can detect when the feeding set is loaded on the pump 501.

The ultrasonic sensor 564 can be operated to detect various conditions of the feeding set loaded on the pump 501. A first sensor pair 507 is positioned on the upstream side of the rotor and a second sensor pair 509 is positioned on the downstream side of the rotor. The dual sensor system provides the capability to distinguish between upstream occlusions, downstream occlusions, and bag empty conditions. For example, when an occlusion occurs upstream of the pump rotor, fluid will be evacuated from the upstream portion of the tube but not from the downstream portion of the tube. In this instance, the pump 501 will continually detect fluid at the second sensor pair 509, but will not detect fluid at the first sensor pair 507. When this sequence occurs, the pump 501 identifies as an upstream occlusion. In the case of an empty bag, fluid will drain out of the upstream portion of the tube then out of the downstream portion of the tube. In this instance, the pump 501 will initially detect fluid at both sensor pairs 507, 509. Next, the pump 501 will observe a period where fluid is detected by the second, downstream sensor pair 509 but not at the first sensor pair 507. Finally, the pump 501 will not detect any fluid at either sensor pair 507, 509. When this occurs, a bag empty error may be generated. When a downstream occlusion occurs, the downstream portion of the tube will expand improving the conductivity of the signal at the second sensor pair 509 through the fluid. In this instance, the pump 501 will detect a significant rise in the sensor signal at the second sensor pair, which is interpreted as a downstream occlusion. Accordingly, the pump 501 has the ability to detect occlusions in real time Additionally, the pump 501 can be configured to detect a first pressure P1, measured by the pressure sensor 530, within a first pressure range for indicating that a feeding set is not installed on the pump. The pump 501 can be configured to detect a second pressure P2, measured by the pressure sensor 530, within a second range for indicating that a feeding set has been installed on the pump but fluid is not flowing through the feeding set. The pump can be configured to detect a third pressure P3, measured by the pressure sensor 530, within a third range for indicating that a feeding set is installed on the pump and fluid is present within the feeding set but is not flowing. The pump 501 can be configured to detect a fourth pressure P4, measured by the pressure sensor 530, within a fourth range for indicating that a feeding set is installed on the pump and fluid is flowing through the feeding set.

The fluid in tube pressure P3 and the fluid flow pressure P4 can also be monitored to determine if an occlusion is present in the tubing. For example, during operation of the pump 501 to deliver fluid through the feeding set, the pressure in the feeding set may rise from the P3 range to the P4 range. During normal operation of the pump 501, stopping operation of the pump to deliver fluid through the feeding set will result in a pressure drop from the P4 range back to the P3 range. If an occlusion is present in the feeding set, the pressure will remain in the P4 range after the pump 501 is stopped. However, this pressure profile may occur even when an occlusion is not present. This is because the fluid flow P4 pressure is based on the properties of the tubing and the fluid being pumped through the tubing. Therefore, aspects such as the fluid thickness, viscosity, and tube size can alter the fluid flow pressure P4. Accordingly, depending on the thickness and viscosity of the fluid, and/or the size of the tubing, the pressure may rise to a level indicative of an occlusion (i.e. within the P4 range) when in fact the fluid flow through the tubing is not occluded. Additionally, the fluid properties of nutritional liquid flowing through the feeding set can also affect the readings from the ultrasonic sensor 564 as air bubbles and solid particles within the liquid can alter the signal readings which can result in false indications.

Using the pressure sensor 530 in combination with the ultrasonic sensor 564 can provide a verification of the presence of fluid in the tubing as well as a verification that an occlusion is present in the tubing after an initial indication is made by one of the sensors. For instance, the ultrasonic sensor 564 can be operated to determine whether fluid is present in the tubing. If the ultrasonic sensor 564 indicates that fluid is present, such as by sensor reading above a predetermined threshold, an initial indication of fluid in the tubing can be made. Following this initial indication, the pressure sensor 530 can then be operated to measure the force exerted by the tubing on the pressure sensor. If a pressure reading of P2 or P3 is measured, the presence of fluid in the tubing can be confirmed by the pressure sensor 530. The pump 501 may provide a correction message or an alert in response to the initial fluid detection by the ultrasonic sensor 564, or only after the pressure sensor 530 verifies that fluid is present in the tube.

More particularly, the pump 501 is configured to run a fluid detection routine (FIG. 11) whereby, at 601, the ultrasonic sensor 564 is operated to emit an ultrasonic signal through a portion of the tubing to determine a condition of the feeding set. If the sensor reading is above a predetermined threshold, the pump provides an initial indication that fluid is present in the tubing, at 603. If the sensor reading is at or below the predetermined threshold, the pump 501 provides an indication that no fluid is present in the tubing, at 605. If the system determines at 603 that fluid is present in the tube, a verification sub routine V is initiated. During the verification routine, at 607, the pressure sensor 530 is operated to measure a force at a downstream portion of the tubing. If the measured force exceeds a predetermined threshold, the pump confirms that fluid is present in the tubing, at 609. The pump may then provide an alert or store within the memory that fluid is present within the tubing. If the measured force is at or below the predetermined threshold, the initial fluid detection indication is not confirmed, at 611. The pump may restart the fluid detection routine or provide an alert that a detection of fluid in the tubing could not be made. Therefore, the pump 501 is configured to undergo a series of steps to provide an initial indication of the presence of fluid in the feeding set, and a secondary indication/confirmation using sensor readings from two different sensor types.

Similarly, an occlusion detection can be performed by first operating the pressure sensor 530 to measure a force at the downstream side of the tubing. If the pressure sensor 530 measures a force profile that is consistent with an occlusion (e.g., a pressure rise from the P3 range to the P4 range during operation of the pump 501, and the pressure remaining in the P4 range after the pump has been stopped for a preset period of time) an initial occlusion detection can be made. The pump 501 may then operate the pressure sensor 530 to provide a verification of the initial occlusion detection. If the reading from the ultrasonic sensor 564 also indicates that an occlusion is present, then the initial occlusion detection is confirmed. The pump 501 may alert a user of the occlusion after the initial occlusion determination from the pressure sensor 530, or only after the confirmation determination by the ultrasonic sensor 564.

More particularly, the pump 501 is configured to run an occlusion detection routine (FIG. 12) whereby, at 701, the pressure sensor 530 is operated to measure the force in the downstream portion of the tube during operation of the pump to deliver fluid through the tubing. If the pressure sensor 530 detects a pressure in the tubing that rises above a predetermined threshold during operation of the pump 501 to deliver fluid and subsequently remains at the elevated pressure after the pump is stopped, the pump provides an initial indication that an occlusion is present in the tubing, at 703. If the pressure sensor 530 detects a pressure that remains below the predetermined threshold or rises above the predetermined threshold during operation of the pump 501 to deliver fluid but then drops below the predetermined threshold once the pump is stopped, the pump provides an indication that there is no occlusion in the tubing, at 705. If the system determines at 703 that an occlusion is present in the tube, a verification sub routine V is initiated. During the verification routine, at 707, the ultrasonic sensor is operated to emit an ultrasonic signal through a portion of the tubing. If a sensor reading above a predetermined threshold is detected by the ultrasonic sensor 564, the pump 501 confirms that an occlusion is present in the tubing, at 709. The pump 501 may then provide an alert or store within the memory that an occlusion is present within the tubing. If the signal reading from the ultrasonic sensor 564 is at or below the predetermined threshold, the initial occlusion detection indication is not confirmed, at 711. The pump 501 may restart the occlusion detection routine or provide an alert that an indication of an occlusion could not be made.

In one aspect of the disclosure, the alert may be visual, auditory or a combination thereof. The visual alert may be provided to a user by the display screen 9 (FIG. 1) and or the LEDs 13, and the auditory alert may be provided to a user by a speaker. The alerts may be provided to a user to correct, fix or adjust issues with the system.

Figure 13C:
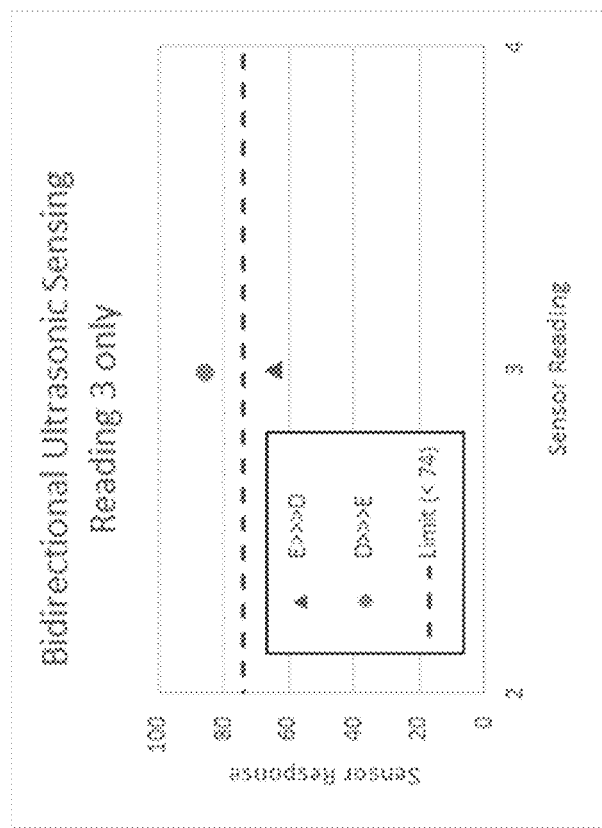
Figure 13B:
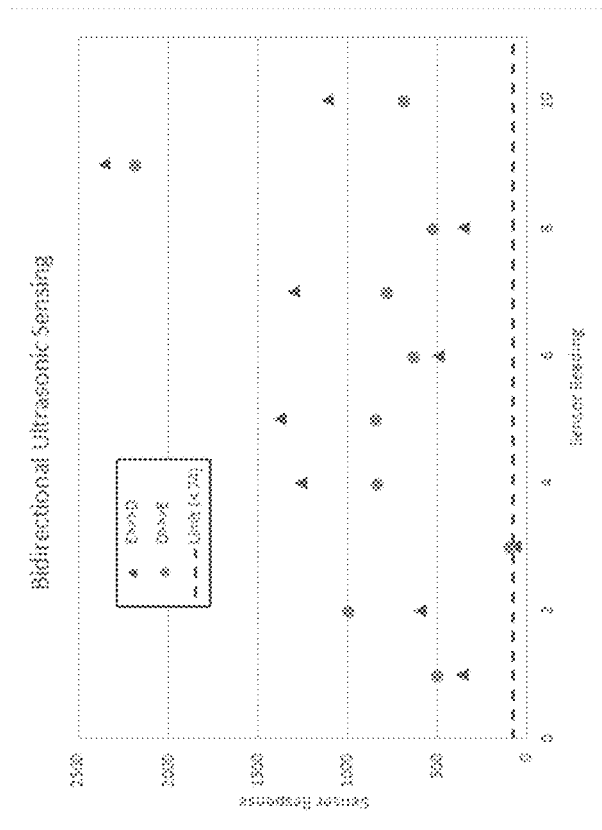

Turning to FIGS. 13A-13C, which illustrate sample results associated with the example illustrations of the skewed tubing received within a sensor track of FIG. 6A and FIG. 6B. Specifically, FIG. 13A illustrates 10 separate tests performed indicating the readings of signal S of the sensor US by switching sides of the emitter and detector. For example, run 1 first provided the emitter operating on the left side of a tube and the detector operating on the right side of the tube, which obtains a value of 358. Run 1 then switched operations of the sensor US, and the emitter is operated on the right side of the tube and the detector is operated on the left side of the tube, which obtains a value of 494. Based on the obtained results, the higher value of 494 is taken by the system and determined that fluid is flow through the tubes. Additionally, as described above, the higher value of the emitter on the right side and the detector on the left side of the tube confirms that tube is biased towards the right side of the tube track, for example as illustrated in FIG. 5C. Runs 2-10 are performed in the same steps. For runs 2, 3, 6 and 8 it can be assumed that the tube is biased towards the right side of the tube track with the operating emitter. For runs, 4, 5, 7, 9 and 10 it can be assumed that the tube is biased towards the left side of the tube track with the operating emitter. FIG. 13B illustrates the results of FIG. 13A in a graph.

FIG. 13C illustrates where the values obtained by the signal S are also compared to a threshold. In accordance with one aspect of the disclosure, the readings obtained by the sensor US must at least meet a minimum threshold value, for example 74, before being considered as a usable value. For example, if both run 3 had readings obtained with a value below 74, the system would immediately determine that an issue has occurred with the system.

The threshold value may be set/determined during the production stage, or during operation to take into consideration the materials of the tube and sensor US, and fluids being passed through the tube.

Figures 14A, 14B:
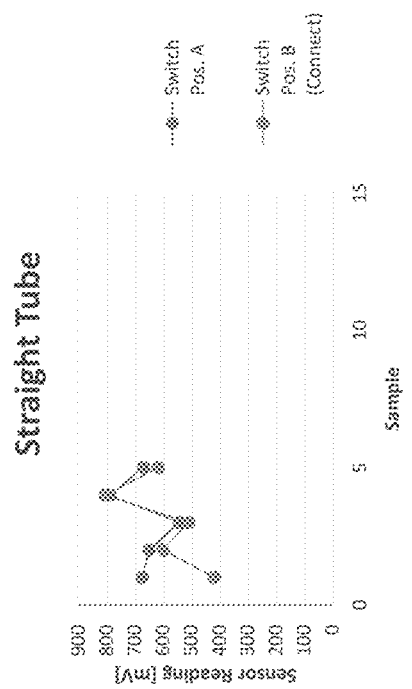
FIG. 14A, FIG. 14B, FIG. 14C, FIG. 14D, FIG. 14E and FIG. 14F illustrate example results associated with the example illustrations of the tubing received within a sensor track in accordance with FIG. 5A, 5B, 5C and FIG. 8.
Figures 14C, 14D:
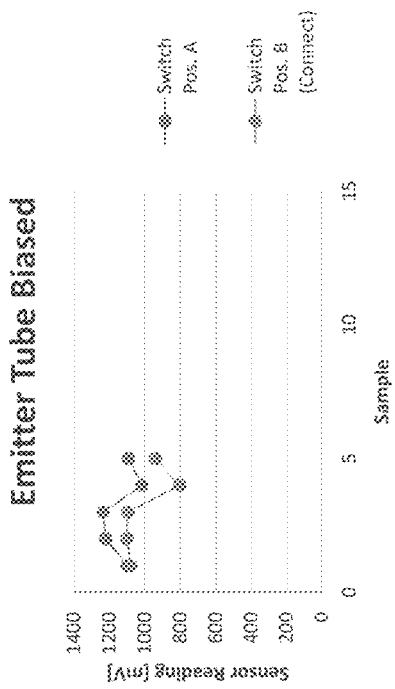
Figures 14E, 14F:
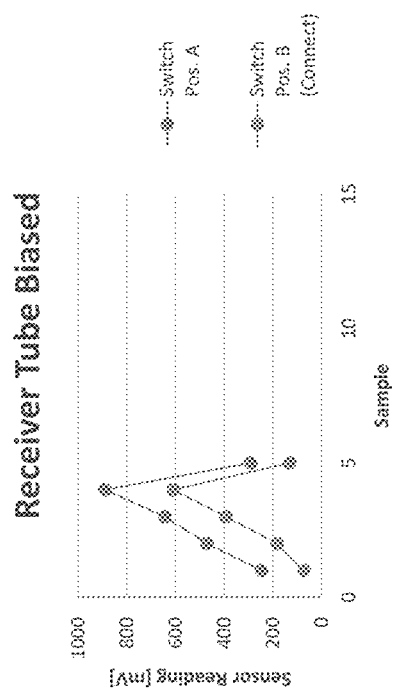

Referring to FIG. 14A, FIG. 14B, FIG. 14C, FIG. 14D, FIG. 14E and FIG. 14F which illustrate sample results associated with the example illustrations of the tubing received within a sensor track in accordance with FIG. 5A, 5B, 5C and FIG. 8. FIGS. 14A-14F illustrate the robustness of the system for acquiring accurate readings as well as the robustness of the overall system. For example, in accordance with one aspect of the disclosure, turning to FIGS. 14A and 14B, runs 1-5 are performed when the tube is properly (centered) within the tube track. Further, runs 1-5 are performed in accordance with the two sensor US positions, A and B, as described above in relation to FIG. 8. For purposes of this example, it does not matter which side of the sensor US is configured to operate as the emitter or detector, as the tube is centered within the tube track. As illustrated in FIGS. 14A and 14B, the max value obtained from the two US positions with a centered tube within a tube track is 805. Further, in accordance with another aspect of the disclose, turning to FIGS. 14C and 14D, runs 1-5 are performed when the tube is biased towards the emitted within the tube track. As described above, runs 1-5 are performed in accordance with the two US positions, A and B, as described above in relation to FIG. 8. As illustrated in FIGS. 14C and 14D, the max value obtained from the two US positions with a biased tube towards the emitter within a tube track is 1235. Further, in accordance with another aspect of the disclose, turning to FIGS. 14E and 14F, runs 1-5 are performed when the tube is biased towards the detector within the tube track. As described above, runs 1-5 are performed in accordance with the two sensor US positions, A and B, as described above in relation to FIG. 8. As illustrated in FIGS. 14E and 14F, the max value obtained from the two sensor US positions with a biased tube towards the detector within a tube track is 891. These results confirm that higher and more accurate readings are obtained when the tube is biased towards the emitter of the US.

Aspects of the present disclosure may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other aspects of the disclosure may include different computer-executable instructions or components having more or less functionality than illustrated and described.

Further, the order of execution or performance of the operations in aspects of the disclosure illustrated and described herein are not essential, unless otherwise specified. That is, the operations may be performed in any order, unless otherwise specified, and aspects of the disclosure may include additional or fewer operations than those disclosed herein. For example, it is contemplated that executing or performing a particular operation before, contemporaneously with, or after another operation is within the scope of aspects of the disclosure.

In operation, the microprocessor 62 executes computer-executable instructions such as those illustrated in the figures to implement aspects of the disclosure. Aspects of the disclosure may also be practiced in distributed computing environments where tasks are performed by remote processing devices linked through a communications network. In a distributed computing environment, program modules may be located in both local and remote computer storage media including memory storage devices.

Figure 15:
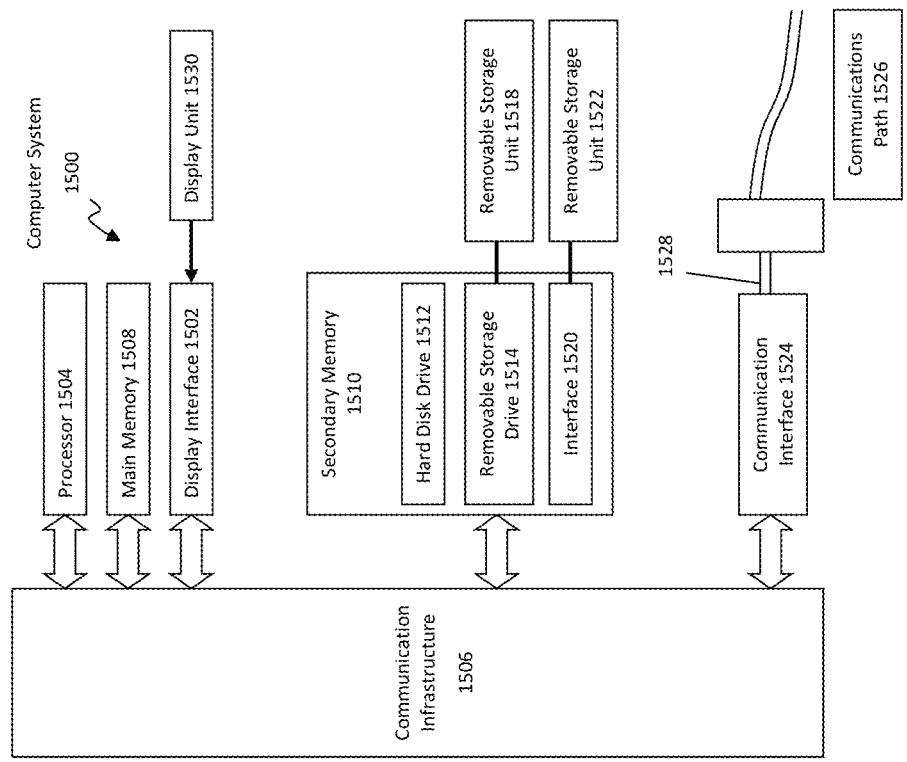
FIG. 15 is an example block diagram of various hardware components and other features of a computer system that may operate the access control system in accordance with aspects of the present disclosure.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. An example of such a computer system 1500 is shown in FIG. 15.

Computer system 1500 includes one or more processors, such as processor 1504. The processor 1504 is connected to a communication infrastructure 1506 (e.g., a communications bus, cross-over bar, or network). Various software implementations are described in terms of this example computer system. After reading this description, it will become apparent to a person skilled in the relevant art(s) how to implement implementations of the disclosure using other computer systems and/or architectures.

Computer system 400 may include a display interface 1502 that forwards graphics, text, and other data from the communication infrastructure 1506 (or from a frame buffer not shown) for display on a display unit 1530. Computer system 1500 also includes a main memory 1508, preferably random access memory (RAM), and may also include a secondary memory 1510. The secondary memory 1510 may include, for example, a hard disk drive 1512, and/or a removable storage drive 1514, representing a floppy disk drive, a magnetic tape drive, an optical disk drive, a universal serial bus (USB) flash drive, etc. The removable storage drive 1514 reads from and/or writes to a removable storage unit 1518 in a well-known manner. Removable storage unit 1518 represents a floppy disk, magnetic tape, optical disk, USB flash drive etc., which is read by and written to removable storage drive 1514. As will be appreciated, the removable storage unit 1518 includes a computer usable storage medium having stored therein computer software and/or data.

Alternative implementations of the present disclosure may include secondary memory 1510 and may include other similar devices for allowing computer programs or other instructions to be loaded into computer system 1500. Such devices may include, for example, a removable storage unit 1522 and an interface 1520. Examples of such may include a program cartridge and cartridge interface (such as that found in video game devices), a removable memory chip (such as an erasable programmable read only memory (EPROM), or programmable read only memory (PROM)) and associated socket, and other removable storage units 1522 and interfaces 1520, which allow software and data to be transferred from the removable storage unit 1522 to computer system 1500.

Computer system 1500 may also include a communications interface 1524.

Communications interface 1524 allows software and data to be transferred between computer system 1500 and external devices. Examples of communications interface 1524 may include a modem, a network interface (such as an Ethernet card), a communications port, a Personal Computer Memory Card International Association (PCMCIA) slot and card, etc. Software and data transferred via communications interface 1524 are in the form of signals 1528, which may be electronic, electromagnetic, optical or other signals capable of being received by communications interface 1524. These signals 1528 are provided to communications interface 1524 via a communications path (e.g., channel) 1526. This path 1526 carries signals 1528 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage unit 1518, a hard disk installed in hard disk drive 1512, and signals 1528. These computer program products provide software to the computer system 1500. Implementations of the present disclosure are directed to such computer program products.

Computer programs (also referred to as computer control logic) are stored in main memory 1508 and/or secondary memory 1510. Computer programs may also be received via communications interface 1524. Such computer programs, when executed, enable the computer system 1500 to perform the features in accordance with implementations of the present disclosure, as discussed herein. In particular, the computer programs, when executed, enable the processor 1504 to perform the features in accordance with implementations of the present disclosure. Accordingly, such computer programs represent controllers of the computer system 1500.

In an aspect of the present disclosure where the disclosure is implemented using software, the software may be stored in a computer program product and loaded into computer system 1500 using removable storage drive 1514, hard drive 1512, or communications interface 1520. The control logic (software), when executed by the processor 1504, causes the processor 1504 to perform the functions described herein. In another aspect of the present disclosure, the system is implemented primarily in hardware using, for example, hardware components, such as application specific integrated circuits (ASICs). Implementation of the hardware state machine so as to perform the functions described herein will be apparent to persons skilled in the relevant art(s).

Figure 16:
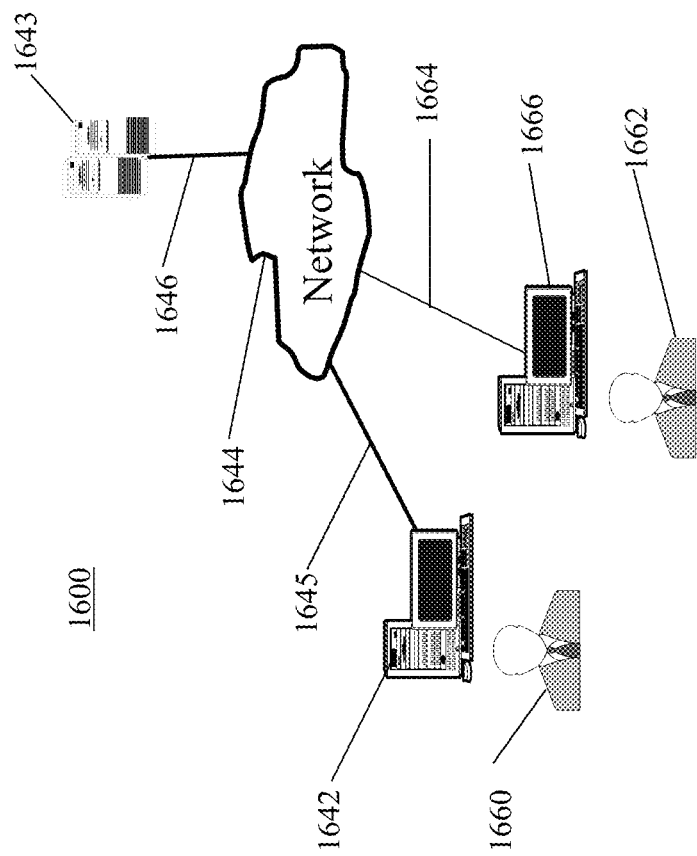
FIG. 16 is a block diagram of various example system components, for use in accordance with aspects of the present disclosure.

FIG. 16 is a block diagram of various example system components, in accordance with aspects of the present disclosure. FIG. 16 shows a communication system 1600 including one or more accessors 1660 (also referred to interchangeably herein as one or more "users"), one or more terminals 1642. Terminals 1642 can include system 100 and or 200, described above, or a related system, and/or the like. In one aspect, data for use in accordance with aspects described herein may be input and/or accessed by accessors 1660 via terminal 1642, such as personal computers (PCs), minicomputers, mainframe computers, microcomputers, telephonic devices, or wired/wireless devices, such as personal digital assistants ("PDAs") and RFID readers (e.g., handheld, mobile, cabinets, etc.) coupled to a server 1643, such as a PC, minicomputer, mainframe computer, microcomputer, or other device having a processor and a repository for data and/or connection to a repository for data, via, a network 1644 for instance, such as the Internet or an intranet, and couplings 1645, 1646, 1664. The couplings 1645, 1646, 1664 may include wired, wireless, or fiber-optic links. In another example variation, the method and system in accordance with aspects described herein operate in a stand-alone environment, such as on a single terminal.

The aspects discussed herein can also be described and implemented in the context of computer-readable storage medium storing computer-executable instructions. Computer-readable storage media includes computer storage media and communication media, and may be, flash memory drives, digital versatile discs (DVDs), compact discs (CDs), floppy disks, and tape cassettes. Computer-readable storage media can include volatile and nonvolatile, removable and non-removable media implemented in any method or technology for storage of information such as computer readable instructions, data structures, modules or other data.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of the processes/flowcharts disclosed is an illustration of example approaches. Based upon design preferences, it is understood that the specific order or hierarchy in the processes/flowcharts may be rearranged. Further, some features/steps may be combined or omitted. The accompanying method claims present elements of the various features/steps in a sample order, and are not meant to be limited to the specific order or hierarchy presented.

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

What is claimed is:

1. A flow control apparatus comprising:
a housing configured to receive a feeding set;
a pumping device configured to produce a fluid flow in the feeding set;
an ultrasonic sensor configured to produce a sensor signal indicative of a condition of the feeding set based on a first ultrasonic signal or a second ultrasonic signal, wherein the ultrasonic sensor comprises a plurality of sensor components, the ultrasonic sensor being further configured to emit the first ultrasonic signal through a portion of the feeding set in a first direction from a first sensor component of the plurality of sensor components, and to emit the second ultrasonic signal through the portion of the feeding set in a second direction opposite the first direction from a second sensor component of the plurality of sensor components; and a control circuit in communication with the ultrasonic sensor configured to receive the sensor signal from the ultrasonic sensor indicative of the condition of the feeding set;

wherein the sensor signal is produced based on a comparison between the first ultrasonic signal and the second ultrasonic signal;

wherein the comparison compares an amplitude of the received first ultrasonic signal and an amplitude of the received second ultrasonic signal, and determines a higher amplitude; and wherein the pumping device is further configured to operate only the first sensor component of the plurality of sensor components or the second sensor component of the plurality of sensor components based on the determined higher amplitude.

2. The flow control apparatus according to claim 1, wherein the control circuit is configured to switch between a first sensor configuration whereby the first sensor component of the plurality of sensor components emits an ultrasonic signal directed to the second sensor component of the plurality of sensor components for detection by the second sensor component, and a second sensor configuration whereby the second sensor component emits an ultrasonic signal directed to the first sensor component for detection by the first sensor component.

3. The flow control apparatus according to claim 2 further comprising a switch connected to the ultrasonic sensor for switching between the first sensor configuration and the second sensor configuration.

4. The flow control apparatus according to claim 1, wherein the plurality of sensor components further comprises a first sensor pair including the first sensor component and the second sensor component for emitting ultrasonic signals between the first sensor component and the second sensor component, and a second sensor pair including a third sensor component and a fourth sensor component for emitting ultrasonic signals between the third sensor component and the fourth sensor component.

5. The flow control apparatus according to claim 4, further comprising one or more switches operatively connected to the ultrasonic sensor for switching between the first direction and the second direction.

6. The flow control apparatus according to claim 5, wherein the portion of the feeding set is a tube.

7. The flow control apparatus according to claim 1, wherein the plurality of sensor components further comprises a third sensor component for detecting the first ultrasonic signal emitted from the first sensor component, and a fourth sensor component for detecting the second ultrasonic signal emitted from the second sensor component.

8. The flow control apparatus according to claim 1, wherein the condition of the feeding set is indicative of at least one of an occlusion of the fluid flow in the feeding set, the feeding set being improperly mounted in the housing, the feeding set being empty, and the fluid flow in the feeding set operating properly.

9. A method of operating a flow control apparatus, the method comprising:

emitting via a first sensor component a first ultrasonic signal in a first direction through a portion of a pump set;

emitting via a second sensor component a second ultrasonic signal in a second direction through the portion of a pump set, the second direction being opposite the first direction;

detecting the first ultrasonic signal to determine a first sensor reading;

detecting the second ultrasonic signal to determine a second sensor reading;

comparing an amplitude of the first sensor reading to an amplitude of the second sensor reading;

detecting a condition of the pump set based on the comparing of the first sensor reading and the second sensor reading;

detecting the condition of the pump set by the flow control apparatus based on a greater reading of the amplitude of the first sensor reading and the amplitude of the second sensor reading; and operating only the first sensor component or the second sensor component based on the greater reading of the amplitude.

10. The method of claim 9, further comprising:
switching between emitting the first ultrasonic signal in the first direction and the second ultrasonic signal in the second direction.

11. The method of claim 9, wherein emitting the first ultrasonic signal in the first direction comprises emitting the first ultrasonic signal from the first sensor component directed to the second sensor component, and emitting the second ultrasonic signal in the second direction comprises emitting the second ultrasonic signal from the second sensor component directed to the first sensor component.

12. The method of claim 9, wherein emitting the first ultrasonic signal in the first direction comprises emitting the first ultrasonic signal between a first sensor pair of components, and emitting the second ultrasonic signal in the second direction comprises emitting the second ultrasonic signal between a second sensor pair of components.

13. The method of claim 9, wherein the portion of the pump set is a tube, and the flow control apparatus provides fluid to a user.

14. The method of claim 13, wherein the condition of the pump set is indicative of at least one of an occlusion of a flow of the fluid in the tube, the fluid being improperly flowing in the pump set, the fluid to the user being exhausted, and the flow of the fluid in the pump set operating properly.

15. A flow control apparatus comprising:
a memory; and
at least one processor coupled with the memory and configured to:
emit a first ultrasonic signal in a first direction through a portion of a pump set;
emit a second ultrasonic signal in a second direction through the portion of the pump set, the second direction being opposite the first direction;
detect the first ultrasonic signal to determine a first sensor reading;
detect the second ultrasonic signal to determine a second sensor reading;
compare an amplitude of the first sensor reading to an amplitude of the second sensor reading;
detect a condition of the pump set based on the comparing of the first sensor reading and the second sensor reading;

detect the condition of the pump set based on a greater reading of the amplitude of the first sensor reading and the amplitude of the second sensor reading; and operate only the first ultrasonic signal in the first direction or the second ultrasonic signal in the second direction based on the greater reading of the amplitude.

16. The flow control apparatus of claim 15, further configured to switch between emitting the first ultrasonic signal in the first direction and the second ultrasonic signal in the second direction.

17. The flow control apparatus of claim 15, wherein emitting the first ultrasonic signal in the first direction comprises emitting the first ultrasonic signal from a first sensor component directed to a second sensor component, and emitting the second ultrasonic signal in the second direction comprises emitting the second ultrasonic signal from the second sensor component directed to the first sensor component.

18. The flow control apparatus of claim 15, wherein emitting the first ultrasonic signal in the first direction comprises emitting the first ultrasonic signal between a first sensor pair of components, and emitting the second ultrasonic signal in the second direction comprises emitting the second ultrasonic signal between a second sensor pair of components.

19. The flow control apparatus of claim 15, wherein the portion of the pump set is a tube, and the flow control apparatus provides fluid to a user.

20. The flow control apparatus of claim 19, wherein the condition of the pump set is indicative of at least one of an occlusion of a flow of the fluid in the tube, the fluid being improperly flowing in the pump set, the fluid to the user being exhausted, and the flow of the fluid in the pump set operating properly.

21. A flow control apparatus comprising:
a housing configured to receive a feeding set;
a pumping device configured to produce a fluid flow in the feeding set;
an ultrasonic sensor including a first sensor component and a second sensor component, the first sensor component configured to emit a first ultrasonic signal through a portion of the feeding set in a first direction and the second sensor component configured to emit a second ultrasonic signal through the portion of the feeding set in a second direction; and a control circuit configured to switch between a first configuration and a second configuration, whereby the first configuration includes the first sensor component emits the first ultrasonic signal directed to the second sensor component for detection by the second sensor component, and wherein the second configuration includes the second sensor component emits the second ultrasonic signal directed to the first sensor component for detection by the first sensor component wherein the ultrasonic sensor is further configured to produce a sensor signal indicative of a condition of the feeding set based on the first ultrasonic signal or the second ultrasonic signal;

wherein the sensor signal is produced based on a comparison between the first ultrasonic signal and the second ultrasonic signal wherein the comparison compares an amplitude of the detected first ultrasonic signal and an amplitude of the detected second ultrasonic signal, and determines a higher amplitude;

wherein the control circuit includes a switch for switching between the first configuration and the second configuration, and wherein the determined higher amplitude is configured to set the switch in only the first configuration or the second configuration for operation of the flow control apparatus.

22. The flow control apparatus according to claim 21, wherein the switch further includes one or more switches operatively connected to the ultrasonic sensor for switching between the first direction and the second direction.

23. The flow control apparatus according to claim 21, wherein the portion of the feeding set is a tube.

24. The flow control apparatus according to claim 21, wherein ultrasonic sensor is further configured to produce a sensor signal indicative of a condition of the feeding set based on the first ultrasonic signal or the second ultrasonic signal.

25. The flow control apparatus according to claim 21, wherein the control circuit is further configured to receive the sensor signal from the ultrasonic sensor indicative of the condition of the feeding set.

* * * * *